US006247004B1

(12) United States Patent
Moukheibir

(10) Patent No.: US 6,247,004 B1
(45) Date of Patent: *Jun. 12, 2001

(54) UNIVERSAL COMPUTER ASSISTED DIAGNOSIS

(76) Inventor: Nabil W. Moukheibir, c/o Connectance, P.O. Box 5632, Washington, DC (US) 20016

( * ) Notice: Subject to any disclaimer, the term of this patent is extended or adjusted under 35 U.S.C. 154(b) by 0 days.

This patent is subject to a terminal disclaimer.

(21) Appl. No.: 09/378,440

(22) Filed: Aug. 20, 1999

Related U.S. Application Data

(63) Continuation of application No. 08/912,718, filed on Aug. 18, 1997, now Pat. No. 6,021,404.

(51) Int. Cl.$^7$ .................................................. G06F 17/00
(52) U.S. Cl. .............................. 706/46; 706/45; 706/47; 600/300
(58) Field of Search ................................. 706/45, 46, 47, 706/50; 600/300; 705/2; 707/1, 100, 200

(56) References Cited

U.S. PATENT DOCUMENTS

| | | | |
|---|---|---|---|
| H958 | * 8/1991 | Devita, Jr. et al. | 365/413.02 |
| 4,796,639 | 1/1989 | Snow et al. | 600/532 |
| 4,839,822 | 6/1989 | Dormond et al. | 706/45 |
| 4,866,635 | 9/1989 | Kahn et al. | 706/46 |
| 5,025,374 | 6/1991 | Roizen et al. | 600/300 |
| 5,172,418 | 12/1992 | Ito et al. | 382/132 |
| 5,255,187 | 10/1993 | Sorensen | 600/300 |
| 5,299,121 | 3/1994 | Brill et al. | 600/301 |
| 5,331,548 | 7/1994 | Rollema et al. | 600/651 |
| 5,341,291 | 8/1994 | Roizen et al. | 600/300 |
| 5,357,427 | 10/1994 | Langen et al. | 600/300 |
| 5,437,278 | 8/1995 | Wilk | 600/425 |

(List continued on next page.)

OTHER PUBLICATIONS

Heinlein et al, "Representation of medical guidelines using a classification based system", ACM CIKM pp 415–422, Mar. 1994.*

(List continued on next page.)

*Primary Examiner*—Mark R. Powell
*Assistant Examiner*—Anh Khatri
(74) *Attorney, Agent, or Firm*—Nixon & Vanderhye P.C.

(57) ABSTRACT

A method is provided which facilitates diagnosis of any describable condition or event. One example is specialty related medical conditions and diseases. The method first provides, in a computer accessible data base, for the creation of a plurality of master maps using keywords and a new diagnostic mapping language. Then a medical description of a patient's history and physical information is input into a computer using simple medical file language. Chemical and test data information are displayed on the screen to prompt entry of available chemical and test data for the patient, and this may also be practiced for imaging selections which may be in a yes/no/empty format. Using a computer processor a data base of specialty medical information is searched to determine the degree of similarity between the information entered and the master maps, and the possible diagnoses are ranked based on the degree of similarity. The three most probable diagnoses are displayed on a monitor, such as in the form of horizontal bar graphics which bar graph is a first color in a horizontal field and the diagnosis corresponding to the bar graph is in the same field in a different color. Biopsy and imaging icons, which are miniature versions of actual biopsies or images exemplary of the disease or condition, may be selected. The computer and data base may be used in a catalog mode, in addition to the above-description analytical mode, by displaying on the screen options relating to the biopsy, imaging, management (a condensed opinion and textual information about how to understand and treat a particular disease or medical condition) and bibliography (a listing of suggested readings).

25 Claims, 13 Drawing Sheets

U.S. PATENT DOCUMENTS

| | | | | |
|---|---|---|---|---|
| 5,463,548 | | 10/1995 | Asada et al. | 600/300 |
| 5,471,382 | | 11/1995 | Tallman et al. | 600/300 |
| 5,517,405 | * | 5/1996 | McAndrew et al. | 706/45 |
| 5,584,297 | | 12/1996 | Bodo et al. | 600/483 |
| 5,594,638 | | 1/1997 | Iliff | 365/177 |
| 5,622,171 | | 4/1997 | Asada et al. | 600/408 |
| 5,687,716 | * | 11/1997 | Kaufmann et al. | 600/300 |
| 5,740,800 | * | 4/1998 | Hendrickson et al. | 600/300 |
| 5,754,850 | | 5/1998 | Janssen | 707/104 |
| 5,772,585 | * | 6/1998 | Lavin et al. | 600/300 |
| 5,778,345 | * | 7/1998 | McCartney | 705/2 |
| 5,784,539 | * | 7/1998 | Lenz | 706/45 |
| 5,806,056 | * | 9/1998 | Hekmatpour | 706/50 |
| 5,812,984 | * | 9/1998 | Goltra | 705/3 |
| 5,839,438 | * | 11/1998 | Graettinger et al. | 600/300 |
| 5,910,107 | * | 6/1999 | Iliff | 600/300 |
| 5,911,132 | * | 6/1999 | Sloane | 705/3 |
| 5,915,240 | * | 6/1999 | Karpf | 705/2 |
| 5,956,689 | * | 9/1999 | Everhart, III | 705/3 |
| 6,016,497 | * | 1/2000 | Suver | 707/103 |
| 6,021,404 | * | 2/2000 | Moukheibir | 706/46 |
| 6,026,363 | * | 2/2000 | Shepard | 705/3 |

OTHER PUBLICATIONS

Fala et al, "Applying expert system to health care management", ACM pp 237–241, 1995.*

Allen et al, "A knowledge based environment for the development of software parts composition systems", ACM pp 104–112.*

Devanbu et al, "Lassie: A knowledge based software infrmation system", IEEE pp. 249–261, Mar. 1994.*

Anderson et al, "Imagine a vision of health care in 1997", ACM, Interchi, p. 535.

Larkey & Croft, "Combining classifiers in text categorization", SIGIR 96 ACM, pp. 289–297.

Gunter et al, "New directions for uncertainty reasoning in deductive databases", ACM pp. 178–187.

Pearl, "Decision making under uncertainty", ACM Com. surveys vol. 28, No. 1, pp. 89–92.

Miller & Larson, An explanatory and argumentative interface for a model based diagnostic system, UIST ACM, pp. 43–52.

Lee et al, "An information model for genome map representation and assembly", CIKM, ACM, pp. 75–84.

* cited by examiner

*Fig. 9*

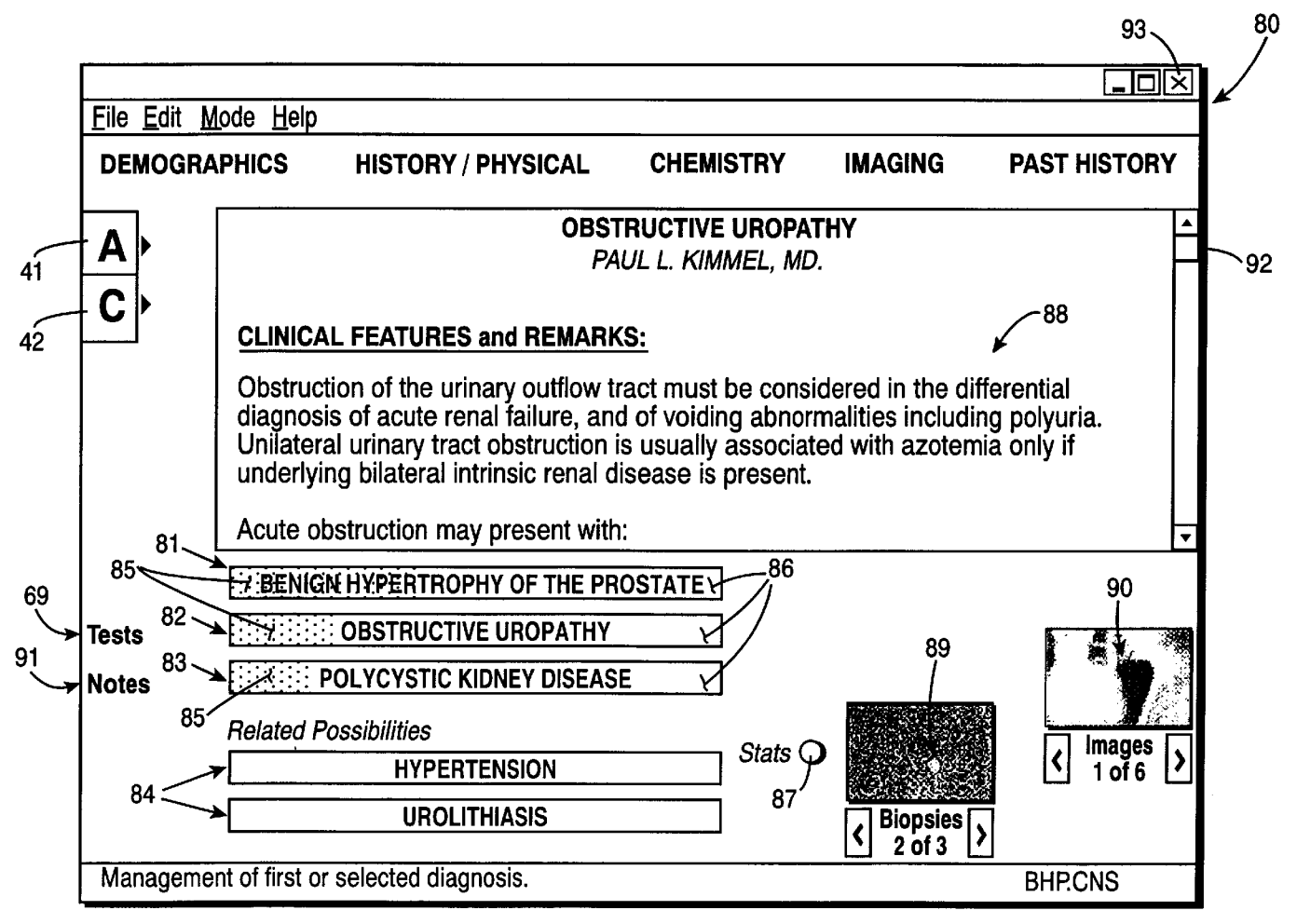

| File Edit Mode Help | | | | |
|---|---|---|---|---|
| DEMOGRAPHICS | HISTORY / PHYSICAL | CHEMISTRY | IMAGING | PAST HISTORY |

OBSTRUCTIVE UROPATHY
*PAUL L. KIMMEL, MD.*

CLINICAL FEATURES and REMARKS:

Obstruction of the urinary outflow tract must be considered in the differential diagnosis of acute renal failure, and of voiding abnormalities including polyuria. Unilateral urinary tract obstruction is usually associated with azotemia only if underlying bilateral intrinsic renal disease is present.

Acute obstruction may present with:

- BENIGN HYPERTROPHY OF THE PROSTATE
- OBSTRUCTIVE UROPATHY
- POLYCYSTIC KIDNEY DISEASE

*Related Possibilities*

- HYPERTENSION
- UROLITHIASIS

Stats

Biopsies 2 of 3

Images 1 of 6

Management of first or selected diagnosis.

BHP.CNS

UNIVERSAL COMPUTER ASSISTED DIAGNOSIS

This is a continuation of application Ser. No. 08/912,718, filed Aug. 18, 1997, now U.S. Pat. No. 6,021,404, issued Feb. 1, 2000, the entire content of which is hereby incorporated by reference in this application.

BACKGROUND AND SUMMARY OF THE INVENTION

In many areas of human endeavor (arts), including medicine (human and veterinary, and particularly specialties therewithin), the biological sciences, geology, automobile repair, etc., it is necessary to diagnose a condition or event from the universe of known conditions or events relating to that art. The use of a computer to assist in that diagnosis has long been considered desirable, and in many art areas computers are used in one form or another to facilitate diagnosis. For most arts, however, truly effective computer utilization to effect diagnosis is still not a reality. In some situations this is due to an inability to effectively use the search and comparison functions of a computer because an appropriate data base is difficult to construct and/or utilize.

According to the most basic aspects of the present invention, a new tool is provided for constructing and utilizing data bases that may be searched and analyzed by a computer in an effective manner, coined "Diagnostic Mapping Language", or DML. The basic concept behind DML is that all events or conditions have characteristic markers that make them unique and therefore identifiable. A novel grammar is utilized so as to build a data base of individual master maps, each master map corresponding to a condition or event to be diagnosed. A diagnosis is secured by a methodical description of its markers, and by utilization of a computer to compare the markers of a condition or event to be diagnosed with the individual master maps to determine the degree of resemblance between the description input and the conditions or events represented by the master maps.

The DML grammar is based upon three classes of words, namely:

Main: word that describes the most important feature of a sentence. In the case of a medical text it may be an organ, a body part, a secretion, a chemical, etc.

Descriptor: a word that further describes the Main word, by adding a qualification.

Complement: a word that further describes the Descriptor by adding a qualification.

In the description of the invention which follows, diagnosis of a human medical condition using a data base containing a plurality of master maps of medical conditions within a particular specialty (such as nephrology) is provided. However, it should be understood that the principles utilized in the examples are applicable to many other arts where a diagnosis is desired, including the veterinary medicine, biological sciences, geology, and automotive repair arts given as examples above. In the examples that follow some features of human medicine interface with computer technology are also provided that are not necessarily based upon the effective utilization of DML to construct and access data bases, but rather have advantages that are applicable to the effective practice of medicine using a computer regardless of the manner in which the data base is constructed or accessed.

According to the broadest aspects of the present invention, a method of creating a computer searchable data base for use with a computer having a display screen, an input device (e. g. keyboard, mouse, voice responsive signal generator, or any other conventional or known device for putting data or commands into a computer), and processor, for ultimately diagnosing a condition or event from a large plurality of possible conditions or events that may exist in a particular art. The method comprises the steps of: (a) Determining what key words (including, possibly, phrases) describe the characteristic features of each of the possible conditions or events of the large plurality of possible conditions. (b) Creating in computer searchable form a master map for each of the large plurality of possible conditions or events using the key words (including, possibly, phrases) from step (a) that accurately describe each of the conditions or events, to provide a data base containing all the master maps. And (c) providing search access to the master maps data base in the computer so that by a user manipulating the input device to provide a narrative containing some of the key words from step (a), the computer processor will compare the key words input to the key words associated with each master map to determine what conditions or events represented by master maps having the highest degree of similarity with the narrative input, and display those conditions or events on the display screen.

Step (a) may be practiced by dividing the key words into three different classifications of words, main words that describe the most important feature of a sentence that accurately describes an aspect of a condition or event, descriptor words that further describe a main word by adding a qualification, and complements that further describe a descriptor by adding a qualification. Step (b) may be practiced by providing a plurality of distinctly searchable elements for each condition, each element including at least a main word, and where they accurately exist, a descriptor and complement associated with that main word. Step (b) may be further practiced by assigning to each of the elements one of at least two possible logics, a first logic that requires a main and at least a descriptor to also be present before the element is recognized by the processor when searching the data base, and a second logic that requires only the main to be present, but recognizes a descriptor and complement if present.

Steps (a) and (b) may also be practiced by assigning key words to laboratory test results related to each condition or event, including the name of a test, the normal numerical value of the test results if the condition or event doesn't exist, and a flag indicating that the value of inputted data is above normal, below normal, or text including at least one of normal, abnormal, positive, negative, absent, or present. Steps (a) and (b) may also further be practiced by assigning either a "yes" or "no" to individual imaging possibilities related to a particular condition.

The art may be a human medical specialty, where the conditions or events are possible diseases or medical conditions of that medical specialty, and where the main words describe the anatomy or body fluid or tissue involved with the disease or medical condition to be addressed, the descriptor describes the deviation from normal of the main word, and the complement adds specificity to the main or descriptor words. In that case, step (c) may be practiced by placing the master maps data base on a CD ROM along with biopsy images, medical imaging images, or both biopsy images and medical imaging images, associated with a plurality of the master maps, the images capable of display on the display screen by the user manipulating the input device.

According to another aspect of the invention, a method of diagnosing a condition or event from a large plurality of possible conditions or events that may exist in a particular art, each condition or event being provided in a master map which describes that condition or event using a plurality of art specific key words, is provided. The method is practiced using a computer having a display screen, input device, and processor, and comprises the following steps: (a) Providing search access to the master maps data base in the computer so that by a user manipulating the input device to provide a narrative containing some of the key words from the master maps, the computer processor will compare the key words input to the key words associated with each master map. (b) Using the input device, inputting a narrative description that can facilitate diagnosis, the narrative description using some of the key words. (c) Using the input device, activating the computer processor to recognize the key words from the input narrative description, compare the key words to the key words of each of the master maps, to determine what conditions or events represented by master maps have the highest degree of similarity with the narrative input. And (d) displaying on the display screen at least the two conditions represented by master maps having the highest degree of similarity with the narrative input.

In the practice of this aspect of the invention, each master map may have key words divided into three different classifications of words, main words that describe the most important feature of a sentence that accurately describes an aspect of the condition or event associated with that master map, descriptor words that further describe a main word by adding a qualification, and complement words that further describe a descriptor by adding a qualification, each master map having a plurality of distinctly searchable elements for each condition or event, each element including at least a main word, and where they accurately exist, a descriptor and complement associated with that main word, some of the key words being weighted but the majority of key words having a common value. In this case, step (c) is practiced by counting the weighted number of key words within searchable elements in each master map which also appear in the narrative input in step (b), the master map having the highest weighted number of key words within searchable elements being determined as having the highest degree of similarity, and the condition or event associated with that master map therefore considered to have the highest probability of being the correctly diagnosed condition or event.

Also according to this aspect of the invention, each master map may have assigned to each of the elements one of at least two possible logics, a first logic that requires a main and at least a descriptor to also be present before the element is recognized by the processor when searching the data base, and a second logic that requires only the main to be present, but recognizes a descriptor and complement if present. In this case, step (c) is practiced by: searching with the processor for those first logic elements identified as corresponding to both main and descriptor key words in the narrative description before selection, and then counting the main, descriptor, and complement words associated with those first logic elements; and searching with the processor for those second logic elements identified as corresponding to a main key word in the narrative description and then counting the main words, and any descriptor or complement words associated therewith, of the second logic elements.

Especially where the plurality of possible conditions or events are medical conditions or diseases in a medical specialty (although applicable to other art areas as well), the data base provided in step (a) may also include key words assigned to laboratory test results related to each disease or medical condition, including the name of a test, the normal numerical value of the test results, and a flag indicating that the value of inputted data is above normal, below normal, or text including at least one of normal, abnormal, positive, negative, absent, or present; and values of yes or no assigned to individual imaging possibilities related to a particular disease or medical condition. In this case step (c) is also practiced by searching the relevant laboratory test results and imaging values. The data base may also include biopsy images, medical imaging images, or both biopsy images and medical imaging images, associated with a plurality of the master maps, the images capable of display on the display screen by the user manipulating the input device. In this case, the method may comprise the further step, after step (d), of using the input device to select biopsy or medical imaging images capable of display associated with the diseases or medical conditions determined as having the highest degree of similarity, and displaying those images on the display screen.

In the practice of medicine, it is of course especially important for a doctor to properly diagnose a disease or a medical condition, and then to prescribe the correct treatment. At intermediary stages it is also necessary for a physician to be able to know what tests (chemical or physical), or what imaging techniques (such as X-ray, MRI, etc.), to employ to ensure proper diagnosis of the disease or condition.

In order to facilitate effective diagnosis of medical conditions and diseases, it has long been considered desirable to be able to employ computer equipment, software—even more desirable than in the other arts discussed above, and data bases to assist a physician. While computer-aided medical diagnostics have been attempted or employed in a wide variety of circumstances, the practical implementation of computer-aided techniques, especially for diseases or conditions that typically can only be diagnosed and effectively treated by a medical specialist (such as a urologist, gastroenterologist, endocrinologist, hematologist, cardiologist, or osteopath), has fallen short of expectations. This may in part be due to the inability to effectively meld medical and computer language or techniques, the inability to provide all of the potential information that would be useful to a specialist in making a diagnosis or in effecting treatment, or the utilization of data bases that are not specialized or complete enough. In any event, the invention seeks to effect practical realization of the utilization of a computer and associated data base for facilitating the diagnosis, and typically subsequent treatment, of diseases or medical conditions.

Although it has broader medical applicability, the invention is particularly designed to be used by a specialist (urologist, osteopath, etc.), and is particularly advantageous because it contains a wide variety and depth of information that, when utilized by a specialist, can very effectively and accurately narrow the particular disease or medical condition that a patient suffers from, while providing other alternative diagnoses. The invention is also advantageous not only because it can accomplish the functions set forth above, but because it can be used as a training tool or resource by a physician to enhance his or her understanding of a wide variety of medical conditions or diseases, how they differ, how to effect treatment once diagnosed, and where to locate worthwhile information which enhances understanding.

In the use of DML to construct medical data bases the "main" words usually describe the anatomy or body fluid or tissue or chemical involved with the disease or condition to be addressed, such as "liver, urine, or biopsy". The "descriptor" usually describes the deviation from normal. For example "enlarged, rapid, decreased". The "complement" adds specificity to the main and descriptor elements, typically being an adjective which enhances understanding of the main or descriptor elements. For example if normal medical file language is that a patient complains of right sided colicky pain and dysuria, the main component would be "sided", the descriptor "pain", and the complement "colicky", all of which might ultimately lead to a diagnosis of nephrolithiasis, acute pyelonephritis, polycystic kidney disease, or the like.

The invention also utilizes chemical or physical test data in addition to patient symptom and sign information, family history, and imaging (such as X-ray, MRI, etc.) data. All data is acted upon by a computer processor to determine degree of resemblance with individual master maps for the possible universe of diseases or conditions. According to the invention all of the information may be prompted and/or displayed in readily viewable and understandable (to a physician) format, and in a manner that allows comparison of actual biopsy or imaging data to known biopsy or imaging data for patients known to have the particular disease or condition diagnosed.

According to another aspect of the present invention a method of facilitating diagnosis of medical conditions and diseases (e.g. specialty related) using a computer having a display screen, input device, and processor, and connected to a data base of detailed medical information (e.g. a specialty data base, such as nephrology including a plurality of master maps, one for each known medical condition to be evaluated), is provided. The method comprises the steps: (a) Using the keyboard, inputting into the computer a medical description of a patient's history and physical information, including signs and symptoms, using simple medical file language. (b) Displaying chemical and test data information on the screen to prompt entry of available chemical and test data for the patient. (c) Using the input device, entering all relevant chemical and test data in response to the prompt from step (b). (d) Displaying a plurality of imaging option selections on the screen in yes/no format. (e) Using the input device, entering known imaging data in yes/no format in response to the display in step (d). (f) Using the processor, searching the data base of detailed (e.g. specialty) medical information to determine the degree of resemblance between the data input and each of the master maps, and ranking the possible diagnoses based upon the degree of resemblance. And, (g) displaying on the screen at least the two (preferably three, with two other possibilities) most probable diagnoses based upon the degree of resemblance determined in step (f), and in order of the degree of resemblance.

Preferably step (g) is practiced to display possible diagnoses in the form of horizontal bar graphics in which the bar graph is a first color in a horizontal field and the diagnosis corresponding to the bar graph is also in the horizontal field in a second color, different than the first color, the length of the bar graphics being proportioned to the probability of the diagnosis.

The method also preferably comprises the further step (h) of displaying at least one of biopsy and imaging icons that may be selected to provide pictorial information displayed on the screen corresponding to a selected one of the diagnoses displayed on the screen. Typically steps (g) and (h) are practiced to highlight one of the diagnoses and to display a biopsy and imaging icon associated with the highlighted diagnosis. Also the method may comprise the further step (i) of automatically displaying on the screen textual information corresponding to the highlighted diagnosis, and allowing the display of additional textual information to be selected; and step (h) is preferably further practiced by displaying the biopsy and imaging icons as actual biopsy and imaging pictorial representations of the diagnosis highlighted, each icon taking up less than one third the screen before selection thereof. The method may also comprise the further steps of providing zoom and marking functions within a displayed biopsy or image corresponding to a highlighted diagnosis upon selection of the biopsy or imaging icons.

The invention also preferably comprises the further step (j) of, in response to a prompt displayed on the screen, inserting historical information into the computer using the keyboard device and step (f may be practiced to use the historical information inserted in step (j) in determining the order of display in step (g).

Steps (b) and/or step (g) are preferably further practiced to display a "TESTS" icon which, upon selection, displays tests to be performed in order to confirm a selected diagnosis. Also preferably steps (d) and (e) are practiced, and the imaging object selection is preferably provided in, yes/no/empty format. That is each imaging option will have a "yes" or a "no" value, or in some selected instances may be "empty" (that is having neither a yes or a no value).

The invention may also comprise the further steps, during the practice of at least one of steps (b), (c), (d) and (e), of displaying an alphabetical keyboard image on the screen, and (n) using the input device, selecting a letter from the alphabetical keyboard image to display on the screen a listing of chemical or test data, or imaging options, starting with the letter selected.

According to another aspect of the present invention a method of facilitating diagnosis of specialty related medical conditions or diseases using a medical data base is provided. The method may comprise the steps of: (a) Using the input device, inputting into the computer a medical description of a patient's history and physical information, including signs and symptoms, and any relevant available chemical and test data and imaging information. (b) Using the processor, searching the data base to determine the most likely possible diagnosis. (c) Displaying on the screen at least the two most probable diagnoses located in step (b). And, (d) substantially simultaneously with step (c), displaying on the screen textual information, and at least one of biopsy and imaging icons, corresponding to a selected diagnosis, the biopsy and imaging icons, if selected, displaying on the screen actual pictorial representations of actual biopsies or images associated with the diagnosis selected.

In this aspect of the invention there preferably is the further step (e) of displaying on the screen, in comparative format, biopsy or imaging pictorial representations corresponding to more than one diagnosis from step (c). Also the details of the particular steps may be generally as described above with respect to the previous aspect of the invention.

The preceding aspects of the invention are primarily related to the analytical techniques that are utilized according to the present invention. While those may be the only techniques utilized, the invention may also be designed so as to additionally (or alternatively) be operable in a catalog mode which does not require the entry of real live information in order to be utilized by a physician and students, but rather may be used by a physician for education or practice diagnoses, i.e. as a resource.

When the catalog aspect of the present invention is utilized, either in addition to or instead of the analytical aspects, there is provided a method of providing specific categorized information relating to medical information using a computer having a display screen, and input device and connected to a data base of medical information. The method comprises the steps of: (a) Displaying on the screen the options of biopsy, imaging, management, and bibliography relating to a particular disease or medical condition. (b) Using the input device selecting the biopsy option to display pictorially on the screen actual biopsy pictorial representations of the particular disease or medical condition. (c) Using the input device selecting the imaging options to display pictorially on the screen actual imaging pictorial representations of the particular disease or medical condition. (d) Using the input device selecting the management option to display on the screen a condensed opinion and textual information about how to understand and treat the particular disease or medical condition. And, (e) using the input device selecting the bibliography option to display on the screen a listing of suggested readings related to pathogenesis and therapy for the particular disease or condition.

According to this aspect of the invention, the invention also preferably comprises a method wherein steps (b) and (c) are further practiced by displaying zoom and marking functions on the screen, and using the input device, selecting the zoom or marking functions to effect increase or decrease in the size of any particular area of the biopsy or imaging pictorial representations displayed, or to effect marking of any desired portion of the biopsy or imaging pictorial representations displayed.

According to another aspect of the invention a method of providing specific categorized information relating to medical information using a computer having a display screen, CD ROM, and input device, and connected a data base of medical information on a CD which is utilizable by the CD ROM, is provided. The method comprises the following steps: (a) Displaying on the screen an analytical option and a catalog option. (b) Using the input device, selecting the analytical option to bring up screens allowing the input of a patient's history and physical information, including signs and symptoms, chemical and test data, and imaging data, that may contribute to an accurate differential diagnosis. (c) Using the input device entering the known information from step (b). (d) Searching the CD data base with the computer to match the information entered with known disease and medical condition information contained in the CD data base. (e) Using the input device, selecting the catalog option to display on the screen options relating to an opinion about how to understand and treat a disease or condition, reading material relating to a selected disease or condition, and at least one of biopsy and imaging information relating to a selected disease or condition. And, (f) using the input device, selectively displaying the at least one of biopsy and imaging information from the CD in pictorial form on the display screen, which biopsy or imaging information relates to a selected disease or condition.

It is the primary object of the present invention to provide effective computer-aided methodology for diagnosis of all types of conditions or events, and particularly all (including obscure, and specialty related) human medical conditions and diseases, as well as providing a practicing specialist or other physician with such detailed information that the computer-aided techniques according to the invention will be effective in virtually all circumstances to greatly facilitate the physician's ability to diagnose, and typically also treat, a medical condition or disease. This and other objects of the invention will become clear from an inspection of the detailed description of the invention and from the appended claims.

BRIEF DESCRIPTION OF THE DRAWINGS

FIGS. 4 through 14 are schematic representations of exemplary screens of data, and/or pictorial representations, that are displayed on the computer screen of the equipment of FIG. 1 when practicing the method according to the present invention.

DETAILED DESCRIPTION OF THE DRAWINGS

In the detailed description that is provided according to the present invention, the invention will be described specifically with respect to the specialty of nephrology, and assuming a Windows® operating system. As indicated earlier, however, the invention is applicable to all medical specialties and many, many art areas. Therefore, this description is only for purposes of facilitating understanding, and does not imply that the invention is restricted to a single art.

The computer programs that are written to implement the invention can typically be built using a combination of multi-media Toolbook™ (for version 4.0) and a visual C++. However it is to be understood that other specialty data bases, or general medical data bases, or other operating systems may be utilized, these specific examples being a representation.

Figure 1:
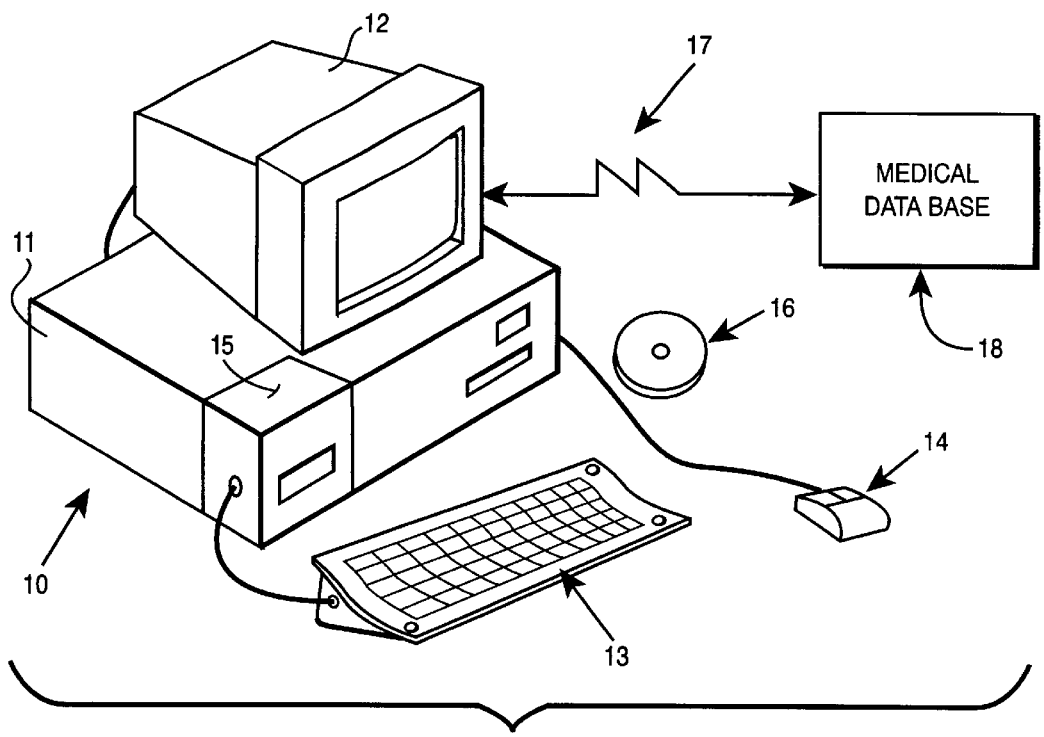
FIG. 1 is a schematic perspective view of exemplary equipment utilized in the practice of the method according to the present invention.

FIG. 1 illustrates, schematically, equipment that is utilized in the practice of the methods according to the present invention. The equipment includes a standard computer 10, such as a PC, including a housing 11 containing a processor. A display screen 12 is provided. Data is input into the computer 10 utilizing any known or conventional input device, such as a conventional keyboard 13, a conventional mouse 14, a voice responsive signal generator, or the like. A CD unit 15 is preferably also provided, which can be built directly into the computer housing 11, and which is adapted to receive a CD ROM 16 containing the software and data base associated with the present invention. Alternatively, or in addition, the computer 10 may be connected up by phone lines 17 (or like data transmission lines) through a modem to a remote medical data base 18.

In order to effectively practice the methods according to the invention, it is preferred that the computer processor in the housing 11 comprise a Pentium CPU, 100 megahertz, that the computer 10 operating system be Microsoft® Windows® (version 3.1 or above), that the computer 10 have eight MB RAM, that the monitor 12 be a super-VGA color monitor (16 bit) at 640×480 resolution, and that the CD ROM 15 be a four speed CD ROM.

Figure 2:
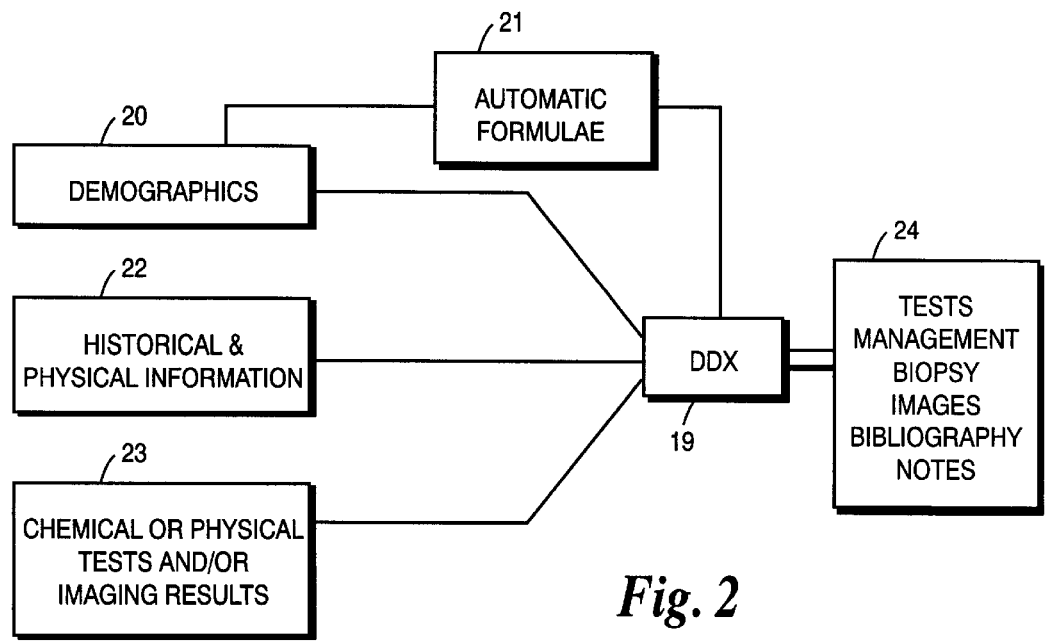
FIG. 2 is a general schematic indicating the major functional components of the system utilized in the use of the invention.
Figure 3:
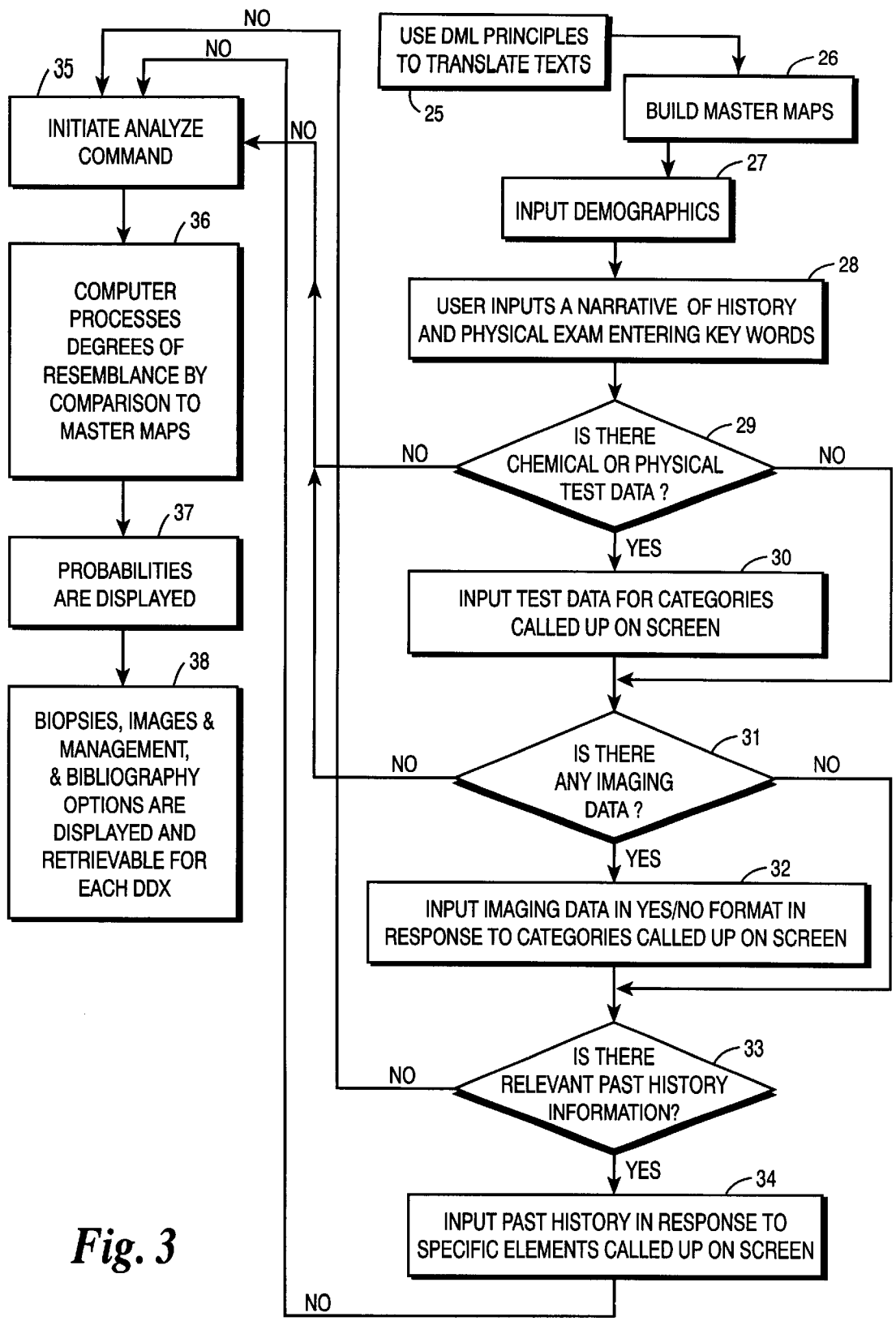
FIG. 3 is a high level flow chart showing an exemplary practice of the method according to the present invention.

FIG. 2 is a schematic representation of the interconnections between the various elements for the analytical mode for the practice of the method according to the claimed invention. As seen in FIG. 3 the general contributors to the differential diagnosis (DDX) 19 that is ultimately achieved include demographics 20 (operating through the automatic formulae 21), historical and physical information 23, and chemical or physical tests and/or imaging results 23. Adjunct utilizations and/or displays that may be utilized according to the invention are also shown schematically as indicated at 24, including tests, management, biopsy, images, bibliography, and notes.

FIG. 3 is a high level flow sheet showing the exemplary practice of all aspects of the method according to the present invention, from creation of the data base, to utilization of a specific data base for both analytical and catalog modes.

The first procedure according to the invention is the use of DML principles to translate texts into a form that can effectively be utilized to facilitate diagnosis, this procedure begin schematically illustrated at 25 in FIG. 3. As earlier described, DML uses main (a word that describes the most important feature of a sentence), descriptor (a word that further describes the main word), and complement (a word that further describes the descriptor by adding a qualification) words. The main, descriptor and complement words (including phrases) are key words that are part of the particular nomenclature or jargon that is used by those working in a particular art, for the examples that follow, for example, nephrologists. The translation provided at 25 needs to be done by a trained professional, such as a nephrologist, or a physician's assistant trained in nephrology.

The next step is to build master maps using DML, as schematically illustrated at 26 in FIG. 3. For the nephrology example that follows, it is assumed that laboratory and imaging results, such as blood chemistry, urine examination, biopsies, and x-ray, MRI, or like imaging of the organs, and the like, are to be utilized in addition to physical examination of the patient. Each master map corresponds to a particular disease or medical condition known in the art area. Each master map will have the name of the disease, and the DML text—written by a specialist—associated with that disease, and put into computer language by a programmer. Each disease will be described by as many lines of code as needed for a complete and adequate description. Each line of code will have at least a main word, and may have a descriptor or complement, and a logic "flag" associated therewith. The diseases of each of the master maps desirably (although certainly not necessarily) are described to the same extent (e.g. the same number of lines of code). If desired, various features (e. g. main words) may be given a higher weight than others, although the majority (typically well over 90%) of the lines and key words will have the same weight (nominally "1"). The number of master maps may range from only a dozen or so to thousands, depending upon the art involved. For example for nephrology, between 100–200 master maps may be necessary to adequately cover the spectrum of conditions and diseases that might be encountered.

A specific example follows regarding the practice of steps 25 and 26 in FIG. 3 for a master map for the medical condition nephrolithiasis:

Text:

"Diagnosis: Nephrolithiasis

The patient complains of abdominal colicky pain and dysuria. Most often, the pain originates from the side where the stone is located.

From the loin, the pain radiates downward and forward. It may reach the testicles or tiD of the Penis. Burning on urination may be present specially in the presence of an infection. If the situation gets complicated, the patient may have fever and chills. If there is no underlying renal disease, the urea nitrogen and creatinine values are normal."

The underlined words are pre-selected by the translator and parsed into the three categories. Example:

The Text translation into DML is:

Disease: Nephrolithiasis

| Main | Descriptor | Complement | Flag |
| --- | --- | --- | --- |
| Pain | Abdominal | Colicky | T |
| Dysuria | | | |
| Penis | Pain | Radiates | T |
| Pain | Radiates | Testicle | T |
| Burning | Urination | | F |
| Fever | | | F |
| Infection | | | F |
| Chills | | | F |

If a Flag T is present: The three words must be present in order to be counted by the computer. The sequence in which they are entered is not relevant to the computer count.

If a Flag F is present: Only the Main has to be present; if however a Descriptor and/or a Complement is/are present, they are recognized and included in the computational system. The order of their sequence becomes important.

Laboratory translation into DML is:

Main=Nephrolithiasis.

Descriptor=Normal Numerical value of the test.

Flag=2 means the patient's value is below Normal.

Flag=1 means the patient has a value above the Normal.

Flag=0 means the patient's value is not digital but text:
  Normal, Abnormal, Positive, Negative, Absent, Present.

In this particular example:

| Main | Descriptor | Value | Flag |
| --- | --- | --- | --- |
| Nephrolithiasis | Urine Albumin | 151 | 2 |
| Nephrolithiasis | Urine RBC | 2 | 1 |
| Nephrolithiasis | Urine WBC | 2 | 1 |
| Nephrolithiasis | RBC Casts | 0 | 2 |
| Nephrolithiasis | Urine Culture | Positive | 0 |
| Etc. | | | |

A DML Description of Imaging results may be as follows:

The imaging results contain a simple Yes/No (or Yes/No/Empty).

Yes=The patient has a specific imaging find.

No=The patient does not have any finding.

The totality of the above represents the Master map for nephrolithiasis.

The other steps in FIG. 3, besides steps 25 and 26, relate to utilization of the master maps which (including associated biopsies, and medical images) are placed on the CD 16, and inserted into the computer 10 (or provided at the central location 18 and accessed using the transmission lines 17).

Step 27 is simply the inputting of demographic information using the input device 13, 14. The next step, 28, is the inputting, using input device 13, 14, of a user narrative. The user is a physician who is familiar with the nomenclature of nephrology, and will—using standard medical file language—use the key words or phrases (main, descriptor and complement) that were used to create the master maps. The narrative, once input, is transformed by the computer 10 into DML, for future analysis, upon selecting the analyze function using the input device 13, 14 (as will hereinafter be described).

An exemplary user's narrative (history and physical examination results in normal language of one in the art) may be as follows (in the example laboratory data and imaging results are also indicated, which would typically be input at 30 and 32, respectively, in FIG. 3, but is provided here for clarity of illustration):

"Patient is a 30 year old man, complaining of severe colicky pain in his right side of three hours duration. There is no previous history of renal disease. The patient started to have nausea and could not tolerate the pain anymore. He describes the pain as tearing and radiating to his testicles. He noticed a definite frequency in his urination and today urination causes burning. His laboratory values are:

Urine RBC's: 20

Urine WBC's: 5

Casts: None

Urine protein: None

Urine Culture: Positive."

Laboratory values as DML:

| Main | Descriptor | Value | Flag |
| --- | --- | --- | --- |
| Nephrolithiasis | Urine Albumin | 151 | 2 |
| Nephrolithiasis | Urine RBC | 2 | 1 |
| Nephrolithiasis | Urine WBC | 2 | 1 |
| Nephrolithiasis | RBC Casts | 0 | 2 |
| Nephrolithiasis | Urine Culture | Positive | 0 |

Medical Imaging Stores (in DML):

| Main | Value |
| --- | --- |
| Hydronephrosis | Yes |
| Small kidney | No |
| Kidney Stones | Yes |

The next procedure in FIG. 3, after entry of the user's narrative history and physical examination is schematically illustrated by decision box 29. If in response to the decision box 29 there is chemical or physical (e.g. blood work, urine examination, biopsy results, etc.) test data to be input into the computer 10, it is input using the input device 13, 14 as indicated at 30 in FIG. 3. If there is not, the next step is box 31. If in response to decision box 31 there is imaging data to be input, then that is input into the computer 10 using the input device 13, 14 as indicated at box 32 in FIG. 3. If there is no imaging data to be input, or after the data has been input, if in response to decision box 33 there is past history information to be input it will be input as indicated at box 34 in FIG. 3. If there is no past history information to be input, or after it is input, then the "Analyze" function may be initiated using the input device, and practiced by the computer processor within the housing 11, as indicated at 35 in FIG. 3.

Upon receipt of the command ANALYZE, the processor scans the User map (narrative, and all lab and imaging data) and distributes each of its key words to all Master maps. Each key word is assigned a value of one. If "no", "none", "neither", or a like negative appears in the text, the processor will not count the key words associated with that negative. Once the scan is over, the points in each Master map array, are added and converted to a percent of the total points of all the Master maps (diagnoses) present. The percentage reflects therefore the degree of similarity of the User map to each of the Master maps, as indicated at 36 in FIG. 3. Upon inputting the command DDX (for differential diagnosis) using the input device 13, 14 the system displays—as indicated at 37 in FIG. 3—on the screen 12 the first three best fits plus an additional two related fits in a descending order of similarity between the User map and the Master maps.

Simultaneously other displays appear on the screen 12, such as Management of the disease, and when applicable Image(s), Biopsy(ies), as indicated at 38.

Typically biopsies, images, management, and bibliography options are displayed on the screen 12 for each of the identified conditions or diseases, as illustrated schematically at 38 in FIG. 3, and each of these are retrievable for each of the displayed possible conditions or diseases. Box 38 also may be the start of implementation of the catalog mode.

Figure 4:
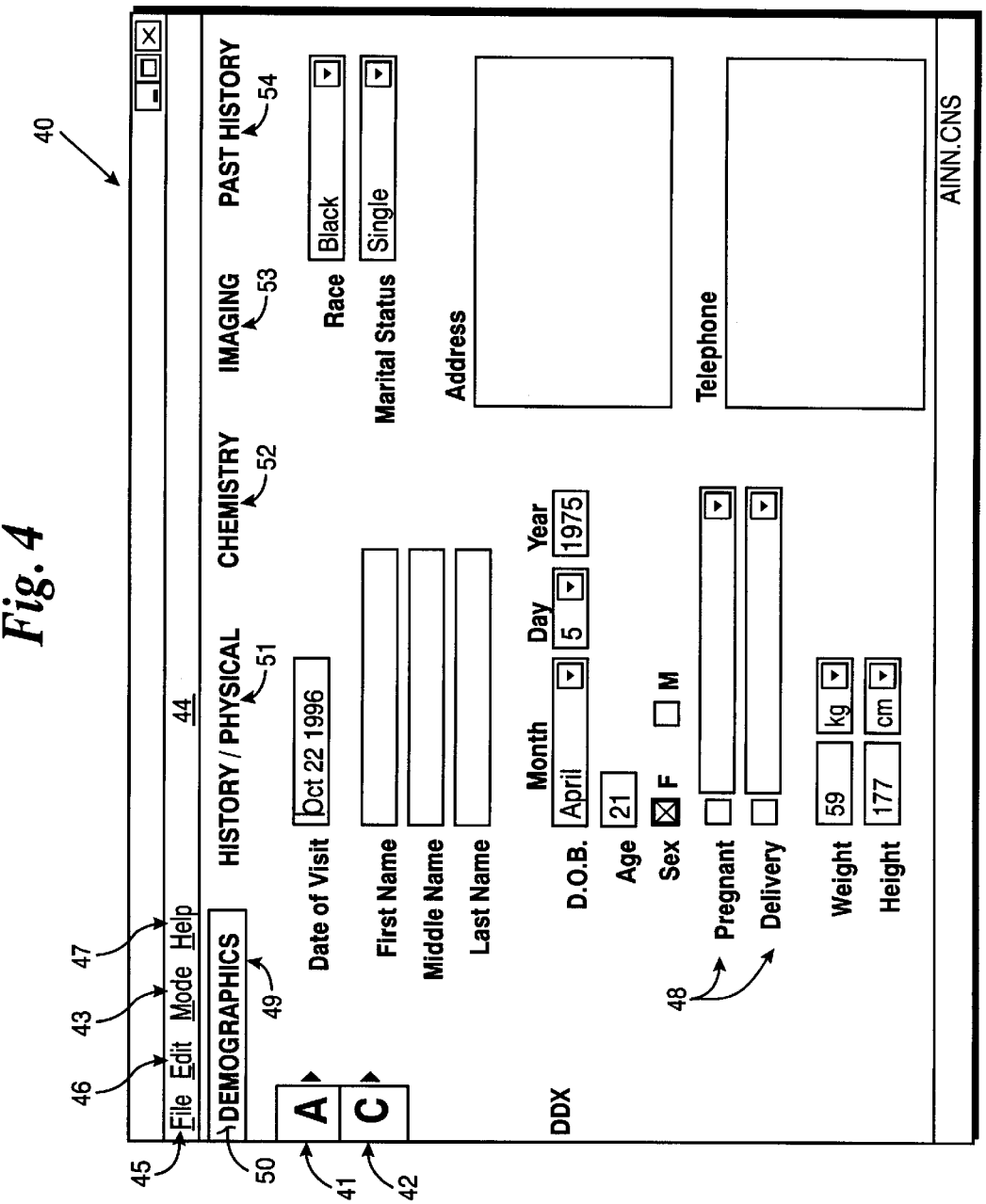

FIG. 4 illustrates an exemplary screen 40 displayed on the monitor 12 when the analysis mode is selected. The displays on the screen 40 that allow selection of either the analysis or the catalog mode, as indicated by the capital letters A and C at 41, 42, respectively. The modes 41, 42 are selected by cursoring to the mode option 43 entry on the menu bar 44 and clicking on (using the mouse 14 or the like, or appropriate keystrokes on the keyboard 13, or using another input device) the desired mode, in the case of the screen 40 of FIG. 4, the analysis mode 41.

The other items on the tool bar 44 for the screen 40, and for many other screens, include as menu items "File" 45, "Edit" 46, and "Help" 47. The File menu item 45 if clicked on using mouse 14 or the like will pop up a window with the standard choices of "new" (to enter a new case *.cns), "open" (to review a previously studied case, and to open a text file *.txt and then save it as a *.cns file), "Save" to save an edited case in the same path, "Save As" to save a case with a different name and/or path, "Print" to print the current page, and "Exit" to exit the program.

The edit menu item 46 pops up a window with the standard choices of "undo", "cut", "copy", "paste", and "clear". The "cut", "copy", or "paste" commands allow one to exchange data between a clipboard and the application at hand. For example text can be copied from the system to any other path in the computer 10. Conversely one can bring in text from anywhere else to the workplace.

The "help" menu item 47, if clicked on, typically displays three components, "contents", which if selected displays the whole body of the "help" text, "search for help on" which pops up a window containing a search mechanism by alphabetical order, or "on-line help" which provides assistance on a page displayed on the monitor 12.

The screen 40 illustrated in FIG. 4 corresponds to the step 27 of FIG. 3. It prompts the entry of personal identification items, some of which are an integral part of the analytical and diagnostic process that will be practiced according to the invention. As indicated on the screen 40, the first visit date, the name of the patient, the patient's date of birth, sex, weight, height, race, marital status, address, and telephone number are prompted and are entered on the screen 40 at the appropriate locations using the keyboard 13, 14. By clicking on the month and day arrow buttons located to the right of the month and day windows, the numbers of the month and days will drop down and may be selected. Once the date of birth information is filled in the age will automatically be calculated. It is important to insert sex and race data because of sex and race linked or high incident diseases or conditions.

Figure 5:
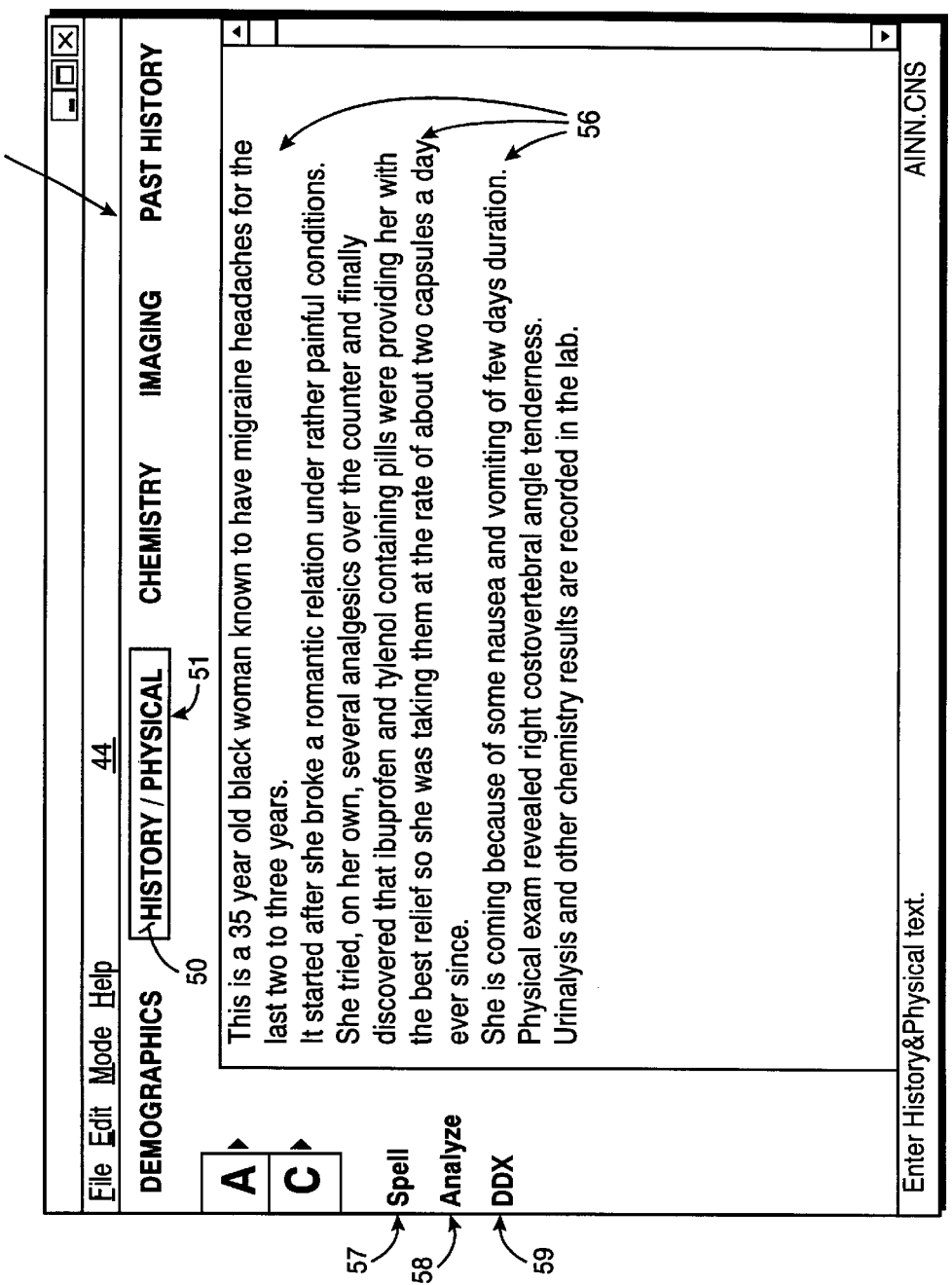

The exemplary narrative ("user map" or "user text") textual information 56 illustrated in the screen 55 in FIG. 5 is entered onto the screen 55, for ultimate entry in the computer 10, by a doctor or his or her assistant in regular standard medical file, describing the results of a physical examination and the patient's history. Standard simple medical terms may be utilized (such as hypertension instead of high blood pressure, or polyuria instead of increased urination). After the data 56 has been entered it is highly desirable to activate the spell check feature 57 before analyzing the data. Short precise sentences should be used, and numerical values avoided. The input of the information 56 is illustrated schematically at 28 in FIG. 3.

The "Analyze" function 58 may be selected at this time, if desired even before screen prompts to enter test data, or the like, as indicated by the left "No" path associated with decision box 29 in FIG. 3. When the "Analyze" function 58 is selected using the input device (e. g. mouse 14), the computer 10 scans the narrative, or "user map", 56 and selects out the key words and distributes them to all of the master maps to determine degree of similarity, as described above with respect to FIG. 3. Also on screen 55 the user may, after selecting the "Analyze" function 58, select the DDX function 59 (using the input device, such as mouse 14), which—as indicated by box 37 in FIG. 3, and as described above with respect to FIG. 3—displays the DDX on the screen 12 (further described with respect to FIG. 9).

Figure 6:
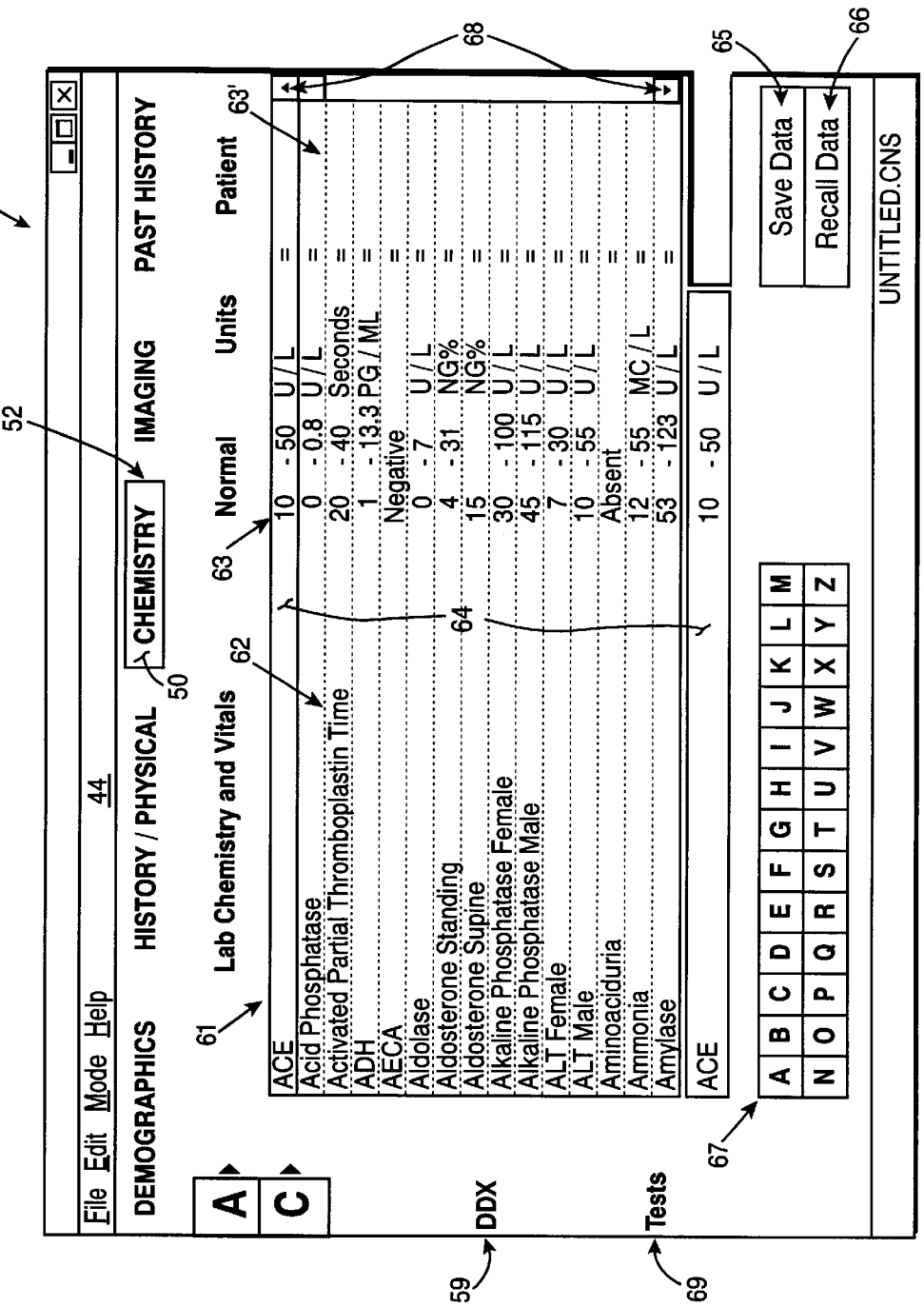

If the doctor has chemical or physical test data (e.g. from laboratory analysis), as indicated by decision block 29 in FIG. 3, then he or she will be prompted to enter that data into the computer 10 when selecting the option 52 using the mouse 14 or the like. This results in the display of the screen 60 on the monitor 12. All known chemical values for blood and urine, as well as blood pressure, pulse and pulmonary artery wedge pressure, are entered on screen 60 using keyboard 13, 14. In the "lab chemistry and vitals" format portion on the screen, indicated generally by reference numeral 61 in FIG. 6, the first column on the left, 62, contains the names of the chemicals to be tested, and vitals. The second column 63 contains the minimum and maximum normal range of the value in standard units. The third column 63' is the space where the value determined by the physician from the physical or chemical test is recorded using the input device (e.g. 13, 14). The cursor is used to move the bar 64 so that it covers a particular horizontal line, which then activates that line and allows the entry of the data in the column 63. By clicking on "save data" 65 the data entry is saved, and by clicking on "recall data" 66 the data is recalled.

Since in the practice of the invention it is highly desirable to provide virtually all chemical or physical values in the column 62 from the data base 16, 18 that might have any relationship whatsoever to the specialty the data base 16,18 deals with, it is desirable to be able to move freely and easily from one section of the tests listings to another. The alphabetical keyboard image 67 (see FIG. 6) is provided to facilitate this. Clicking on any letter on the keyboard 67 with the mouse 14 or the like will put the user on the first item of the list starting with that letter. Scrolling is also possible utilizing the conventional scrolling arrows 68. In the rare circumstance where there is no listing in column 62 for something starting with the letter selected on the alphabetical keyboard image 67, a tone will be heard.

The screen 60 also includes the "tests" option 69. Clicking on the tests option 69 with the mouse 14 or the like displays tests to be performed in order to confirm a preliminary or trial diagnosis. Clicking on the option 69 calls up a window "suggested tests" which contains the name of a disease or condition given in a preliminary diagnosis which may be achieved by clicking on the DDX option 59 in FIG. 5. This window also contains a list of tests, lab and imaging, that may be done for the disease or condition under consideration. This window typically also will have a search option which allows one to pop up another window to search for the tests of a specific diagnosis, that allows you to select your diagnosis of search. Clicking once on an "OK" button will close the window.

Figure 7:
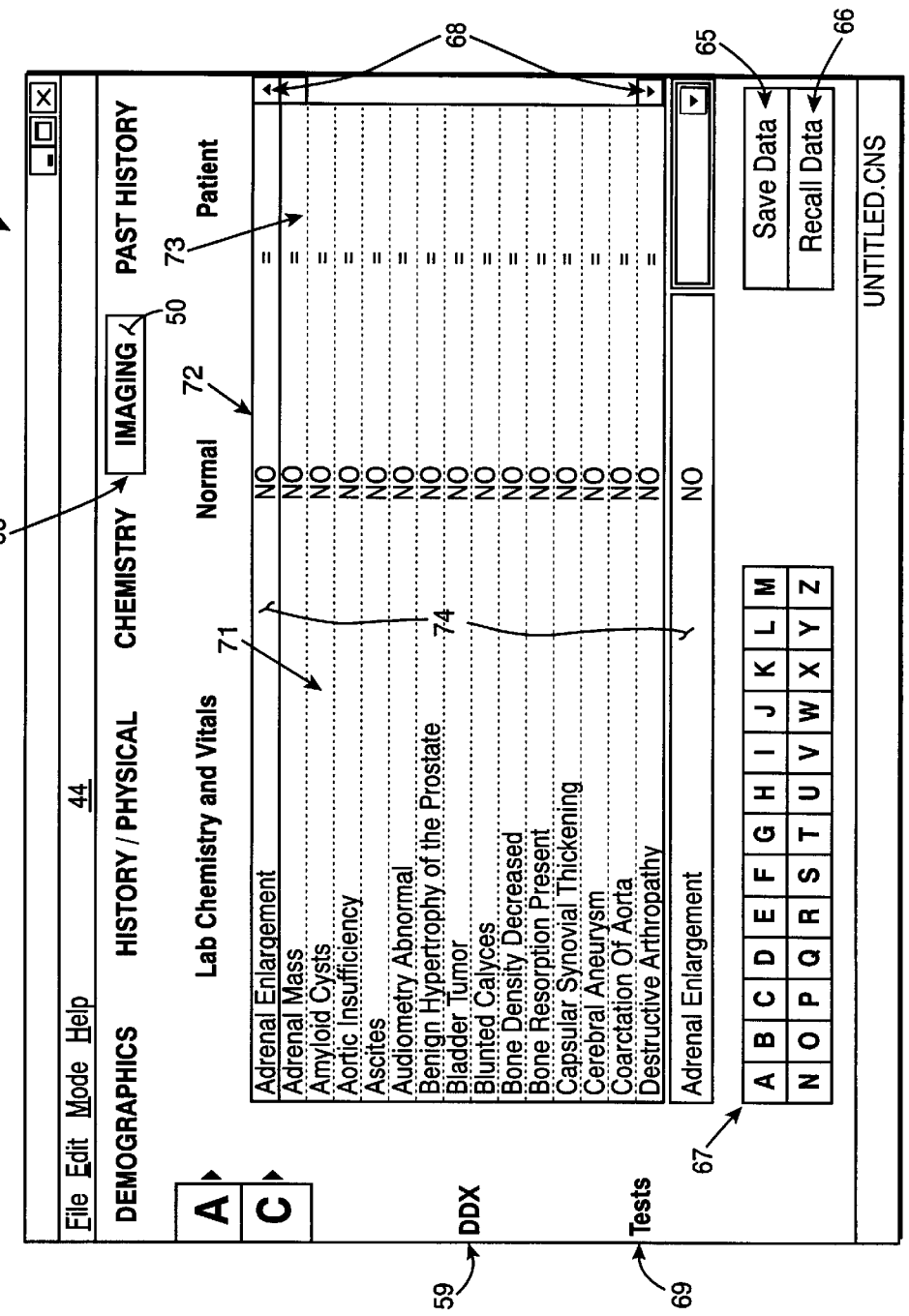

After the appropriate test data has been entered on the screen 60, the DDX option 59 may be activated, or—if as schematically illustrated by decision box 33 in FIG. 3—there is imaging data relating to the patient, that data may be input as schematically indicated at 34 using the screen 70 illustrated in FIG. 7. The screen 70 is displayed on the monitor 12 when the imaging option 53 is selected using the mouse 14 or a like input device. The screen 70 includes the same option/features 59, 65–69, as does the screen 60.

While the method according to the invention may allow for the scanning of imaging data directly into the computer 10, for analysis by computer, for the screen 70 illustrated in FIG. 7 diagnostic information relating to imaging (which could include X-rays, MRIs, sonograms, or any other conventional imaging data) corresponding to the image is in textual form. This allows simplicity of data entry and use. The textual format is typically one which has either "yes/no" or "yes/no/empty" format. The column 71 indicates an image characteristic, the column 72 indicates the normal value for that feature, while the column 73 is where the appropriate data associated with the patient of interest is entered using the input device 13, 14. What is highlighted by the upper bar 74 is repeated at the bottom indicated by the bottom bar 75, and in the column 73 of that bottom bar is where the appropriate value associated with the patient of interest is entered. For example if imaging of the patient of interest shows adrenal enlargement then "yes" is entered in column 73 when the screen 70 exactly as illustrated in FIG. 7 is displayed.

Figure 8:
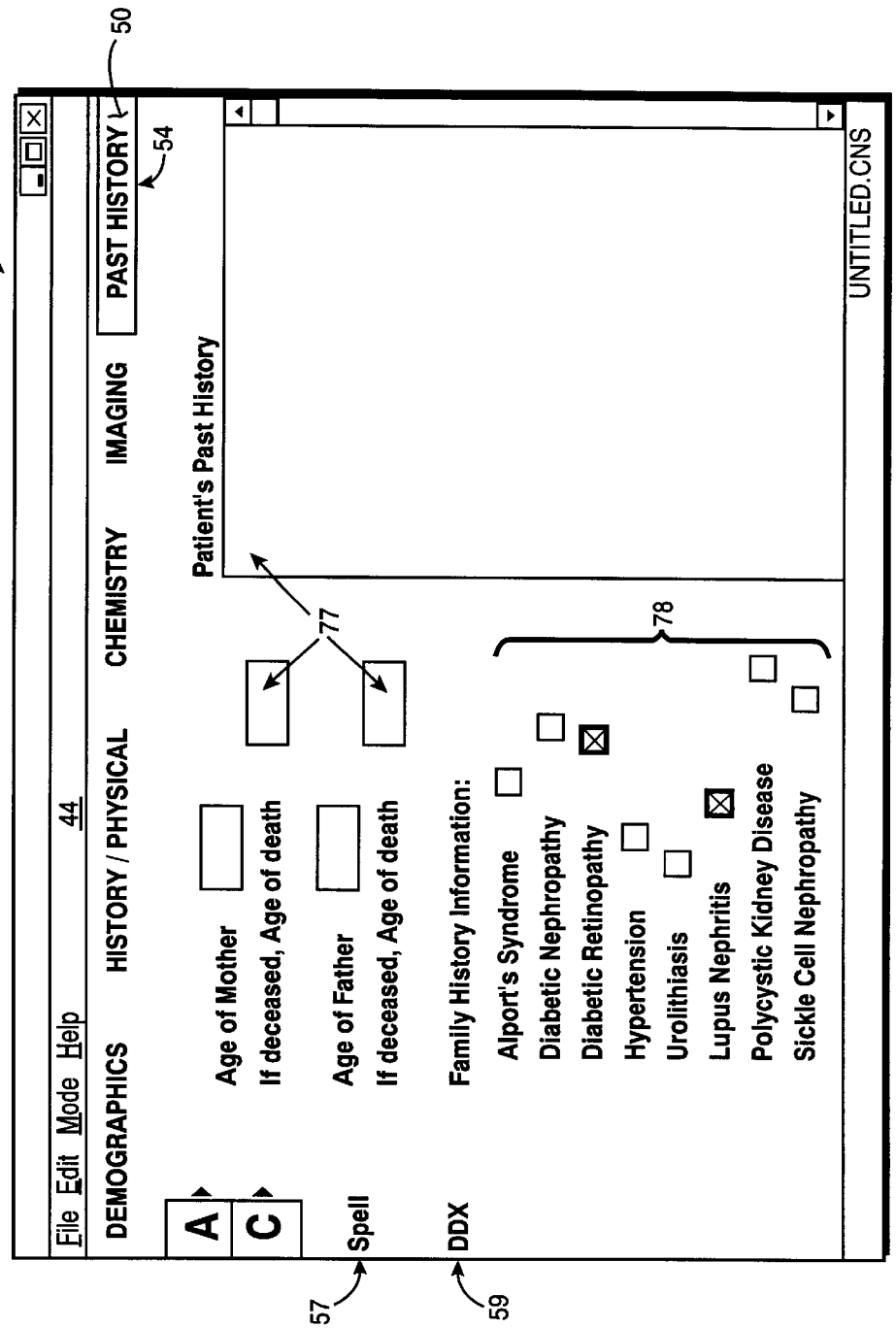

After entry of all of the known data on screen 70 associated with imaging, if as schematically illustrated by decision box 33 in FIG. 3 there is past history data to be entered then entry is made as indicated at 34 in FIG. 3. This is effected by selecting option 54 on the screen 70 (or on an earlier screen containing that option), as illustrated by exemplary screen 76 in FIG. 8. The screen 76, when displayed on monitor 12, contains various areas 77 for entry of family history information that may be of interest to medical personnel, but typically does not form part of an analytical process in the practice of the method according to the invention. However there are some fields 78—that will vary depending upon the general type of medical technology that the data base 16, 18 deals with—where information useful in the analytical process may be entered. The family history conditions 78 illustrated on the screen 76 in FIG. 8 are (as were the specifics of the other screens 60, 70) related to nephrology. Data is entered here merely by clicking on (with mouse 14) the white box associated with each of the elements 78, as illustrated for the entry "Diabetic Retinopathy" in the example of FIG. 8.

By selecting the option 59 for any screen in which it is displayed (e.g. for screen 76), as indicated schematically at 37 in FIG. 3 the computer will display the DDX on the monitor 12, as illustrated by screen 80 (on monitor 12) in FIG. 9. The manner, detail, and extensiveness of the display for the screen 80 as illustrated in FIG. 9 is highly advantageous for the correct, simple, and quick review of the computer calculated diagnosis of diseases or conditions according to the method of the present invention.

On screen 80 at least two, and preferably three (or possibly more), potential diagnoses are displayed as illustrated at 81 through 83 in FIG. 9. These elements 81–83 are referred to as DDX bars. The bars 84 are related possibilities bars. The bars 81–83 list the most likely diagnoses in a descending order of probability. Each bar 81–83 includes actual textual information as well as a bar graph 85 of a different color than the background 86 associated with each of the bars 81–83. For example the bar graphs 85 may be light blue in color while the backgrounds 86 are white, and the textual information is in black. The length of each of the bar graphs 85 is directly proportional to the probability that the particular condition or disease contained in the bar 81–83 in text is the correct diagnosis based upon a comparison of all of the data input to the data in the data base 16, 18. An empty bar may appear where the diagnostic choice is not wide enough.

The screen 80 also includes the statistics option 87. By clicking on the option 87 utilizing the mouse 14 or the like, the numerical values of the first three diagnoses 81–83 will be displayed, in percent, in a descending percentage of diagnostic probabilities. For example for the bar graphs 85 for the bars or horizontal fields 81 through 83 illustrated in FIG. 9, the statistical probabilities may be 50% for benign hypertrophy of the prostate, 30% for obstructive uropathy, and 20% for polycystic kidney disease.

In the preferred embodiment of the invention, the probabilities for the three diagnosis 81–83 will add up to 100% because after the processor of the computer 10 determines the degree of similarity of the data input on the screens of FIGS. 5–8 it will select the top three and recalculate for those three. For example if the master map for benign hypertrophy of the prostate (81) has 10 matches of key words and values with the data input on the screens of FIGS. 5–8, the master map for obstructive uropathy (82) has 6, and the master map for polycystic kidney disease (83) has 4, the computer will add up 10+6+4=20, and divide each number of matches by 20 to get the percentage (e. g. 10/20=50% for 81). However, if it is desired for some purposes to display the total percentage based upon the number of matches for all the master maps, not just the three most likely, that can easily be accomplished.

The "Related Possibilities" bars 84 may also have graphical representations, but in the preferred embodiment illustrated in FIG. 9 merely have the names of the diseases or conditions that are next most likely aside from those displayed in bars 81–84.

When the screen 80 first comes up textual information is displayed in area 88, biopsy pictorial representations in area 89, and images in area 90 corresponding to the diagnosis in field 81. However any of the other fields 82–84 may be selected merely by clicking on the area of the field, which will then display information in areas 88–90 corresponding to the selected diagnosis or possibility. By selecting the tests option 69 the same functions can be performed as earlier (that is a display of suggested tests associated with the diagnosis of interest), and selection of the option 91 may provide "notes" that are of particular interest to the practitioner dealing with that disease or condition, such as food or lifestyle items for the patient to avoid, treatment possibilities, medicines to be prescribed, etc. The textual field 88 will include information for every possible disease or medical condition within the data base 16, 18, but a note option 91, or biopsy or imaging data (or icons) 89, 90, may not be available for all possible conditions or diseases.

By clicking in on the textual field 88 (also called the "Management" field) information will be provided that is highly relevant to the diagnosis. For example the title and author of a medical journal article or the like directly dealing with the subject, and clinical features and remarks will be provided. For example by clicking on the button 92 using the mouse 14 or the like a window will pop up on the monitor 12 that offers as choices "title and author" (clicking on this option will take one directly to the title and author of the article of relevance), "clinical features" (clicking on this option will take one directly to the clinical features section of the diagnosis), "laboratory findings" (clicking on this option will take one directly to the laboratory findings of the selected diagnosis), "management" (clicking on this option will take one directly to the management of the selected diagnosis), and "suggested readings" (clicking on this option will take one directly to articles related to the selected diagnosis).

If instead of clicking in field 88 (or on button 92) one clicks on the biopsy icon 89, a substantially full screen image (or at least much larger image than on the icon 89 itself, in pictorial format, of an actual biopsy from the data base 16, 18 of tissue from someone known to have the disease or condition of interest, will be displayed on monitor 12. Note that the icon 89 itself actually is a small (always less than a third of the entire screen 80, but typically less than 10% of the screen 80) actual pictorial image of a real biopsy. This allows the user to see if there really is any biopsy data associated with the condition or disease. To remove the biopsy pictorial representation (or representations since there may be a number of screens associated with the biopsy that one can go to) one clicks on the "X" button 93 (using mouse 14) on the screen 80. Clicking on the icon 89 with the left button of the mouse 14 will get a half-screen image. At the bottom of each biopsy pictorial representation there is an appropriate caption highlighting the main features of the biopsy.

The image icon 90, and the operation thereof, is exactly the same as for the biopsy icon 89 except that image data (such as X-ray, MRI, sonogram, etc.) is pictorially represented and displayed on monitor 12 rather than biopsy pictorial representations.

At any time the catalog mode 42 may be selected as opposed to the analysis mode 41. This may be done before or after the screen 80, but if done in association with the screen 80 then the data initially presented will correspond to the diagnosis highlighted on the screen 80.

Figure 10:
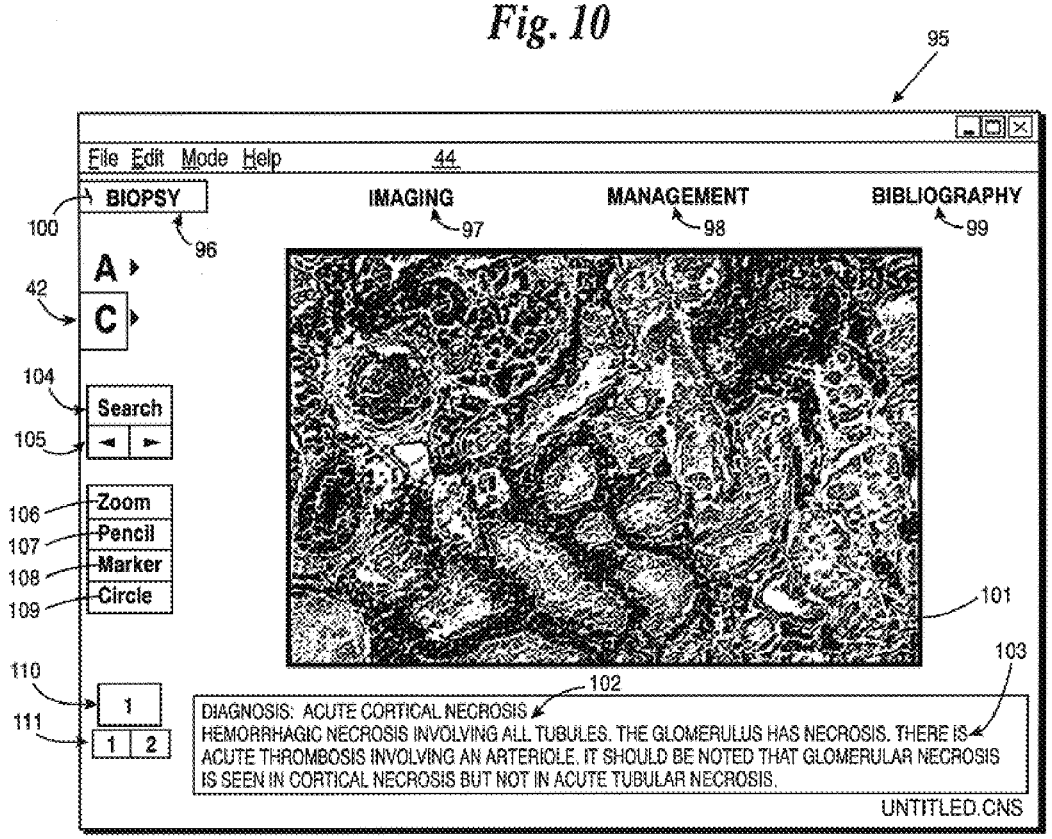

FIG. 10 illustrates a screen 95 displayed on the monitor 12 when the catalog option 42 is selected from a screen like the screen 80. The major options provided are biopsy (96), imaging (97), management (98), and bibliography (99). When a particular option has been selected it is highlighted by a colored background 100 as illustrated for the biopsy option 96 in FIG. 10.

FIG. 10 illustrates an actual pictorial representation 101 of a biopsy for the condition diagnosed as indicated by the text 102 at the bottom of the pictorial representation 101. Other text 103 at the bottom of the pictorial representation 101 sets forth the most important features of the biopsy 101.

The various features of a biopsy screen 95 in the catalog mode are as seen in FIG. 10—search 104, with forward and reverse arrows 105, zoom 106, and various marking functions here designated as pencil 107, marker 108, and circle 109. The function 110, when activated by clicking on with a mouse 14 or the like, provides a single pictorial representation of the biopsy on the screen, as illustrated at 101 in FIG. 10. Clicking on the option 111 provides for two biopsies displayed at once on the screen 95, on the monitor 12. Thus, in the catalog mode the user may have a controlled study of biopsies at will, and with great speed. Biopsies can be viewed one by one (option 110), or two by two (option 111) (the latter offering the opportunity to carry out comparative studies).

Any one of the marker options 107–109 may be selected by pressing the left mouse button 14 while the cursor is on the function 107–109, and pressing the right mouse 14 button will cause the marker to be eliminated. When the "zoom" 106 is selected by pressing the left mouse 14 button, the picture 101 will be magnified; pressing on the right mouse 14 button will downsize the pictorial representation 101 back to normal. Selecting the zoom feature 106, and double clicking on the left mouse 14 button, will enlarge the picture 101 to cover the entire screen 95.

Figure 11:
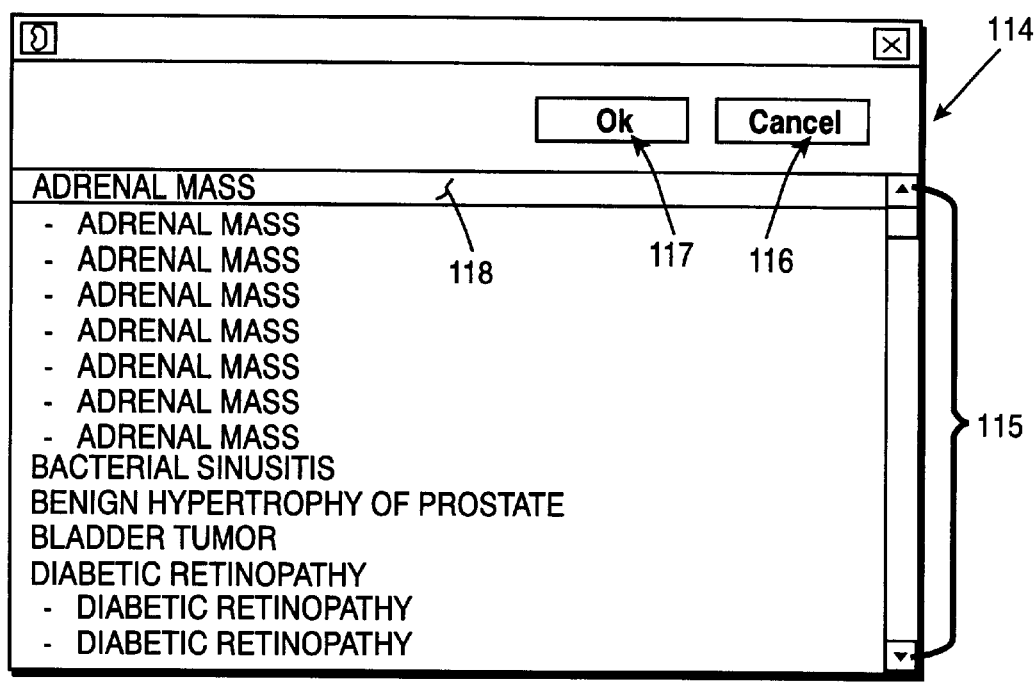

Clicking on the search function 104 facilitates the finding of the specified topic whether the name of a diagnosis, or management or image representation. Clicking on the search button 104 will pop up a window containing a list of diagnoses or management or image representations, such as illustrated for the screen 114 in FIG. 11. One may move through all of the listed diagnoses, etc., using the cursor arrows 115, and either cancel a selected diagnosis using the button 116, or accept it using the button 117. The diagnosis to be accepted by clicking on the highlighted bar representation 118, as seen in FIG. 11.

While a variety of different markers 107–109 may be utilized, the particular markers illustrated schematically at 107 through 109 in FIG. 10 may be indicated as follows: the "pencil" option 107 allows one to draw a line or any other shape. Selecting the option 107 turns the cursor into a pencil ready to draw. "Marker" 108, allows one to pinpoint a discrete detail. Selecting the marker 108 causes a triangle to appear at the point where the cursor is directed on the pictorial representation 101. Clicking on the "Circle" option 109 causes a circle to appear where the cursor is, to encompass an area of interest.

Figure 12:
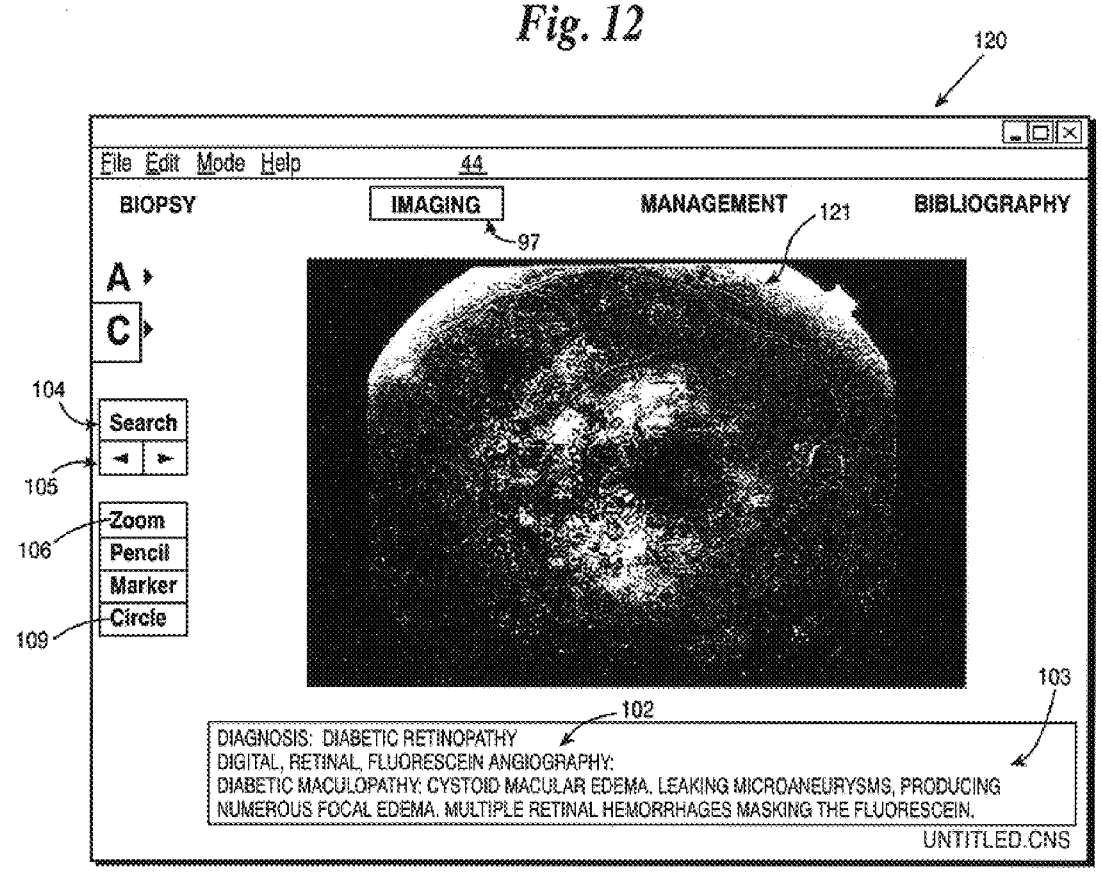

FIG. 12 shows a screen 120 that is the same as the screen 95 of FIG. 10 except that the imaging option 97 (or the imaging icon 90 in FIG. 9) has been selected. The pictorial representation 121 displayed thereon is therefore an image such as from an X-ray, MRI, sonogram, or other imaging technique. The operation of the various functions associated with the screen 120 are essentially identical to those associated with the screen 95. Again below the pictorial representation 121, diagnosis information 102, and other text 103, is provided.

Figure 13:
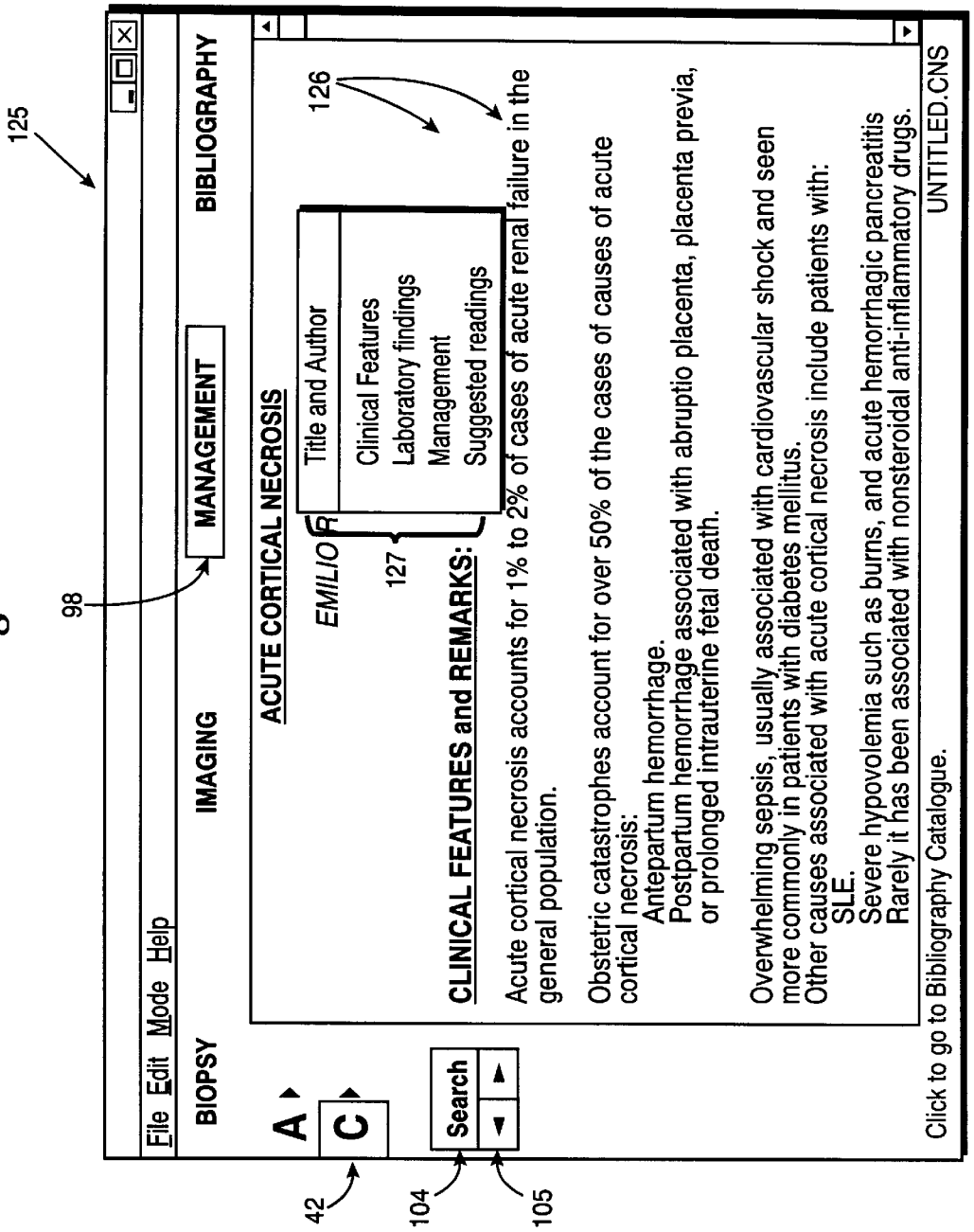

FIG. 13 illustrates a screen 125 like the screens 95, 120 except that the management function 98 has been selected. The data 126 appearing in the screen 125 is a condensed opinion about how to understand and treat the disease or condition. The format provided is that of a hospital-like consultation. Users interested in a more exhaustive study are invited to read the suggested readings that are provided at the end of each management screen 125. Various portions of the management screen 125 may be accessed quickly by placing the cursor on the appropriate entry in the table or window 127 and clicking on (with the mouse 14) the particular element desired (such as "suggested readings") which then takes the screen 125 directly to that portion of the condensed opinion. Alternatively, or in addition, the search function 104, 105 can be used in the same manner as for the screen of FIG. 10.

Figure 14:
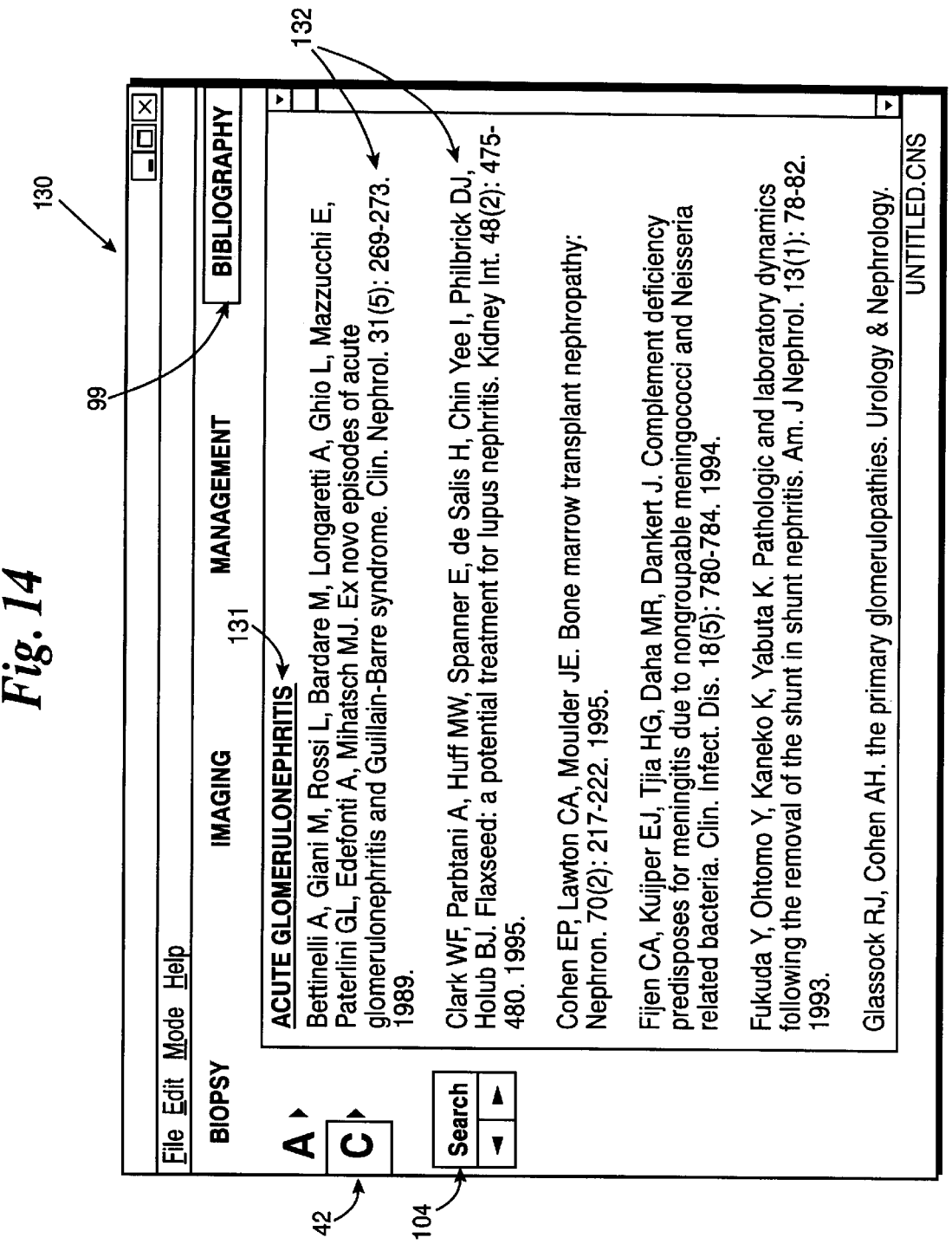

FIG. 14 shows a screen 130 that is the same as the screens illustrated in FIGS. 10, 12, and 13 except that the bibliography function 99 has been selected. This provides a more detailed listing of articles that relate to the condition or disease, the condition or disease being displayed at the top of the text as indicated at 131 in FIG. 14, and the various articles or other texts being listed as indicated at 132, preferably in alphabetical order by the primary authors last name, and with all the necessary information in order for them to be properly retrieved.

It will thus be seen that according to the present invention a highly effective medical differential diagnosis method and system are provided which contain a great deal of worthwhile information, provide ready access to the information, and display the information in readily recoverable form; and, according to broader aspects of the invention, a unique method by using a new "language/grammar" is provided to allow computer-assisted diagnosis in many arts. While the invention has been herein shown and described in what is presently conceived to be the most practical and preferred embodiment thereof. However many modifications may-be made thereof within the scope of the invention, which scope is to be accorded the broadest interpretation of the appended claims so as to encompass all equivalent methods and systems.

What is claimed is:

1. A method of creating a computer searchable data base for use with a computer having a display screen, input device, and processor, for ultimately diagnosing a condition or event from a large plurality of possible conditions or events or events that may exist in a particular art, said method comprising the steps of:
   (a) determining what key words describe the characteristic features of each of the possible conditions or events of the large plurality of possible conditions or events;
   (b) creating in computer searchable form a master map for each of the large plurality of possible conditions or events using the key words from step (a) that accurately describe each of the conditions or events, to provide a data base containing all the master maps; and
   (c) providing search access to the master maps data base in the computer so that by a user manipulating the input device to provide a narrative containing some of the key words from step (a), the computer processor will compare the key words input to the key words associated with each master map to determine what conditions or events represented by master maps have the highest degree of similarity with the narrative input, and display those conditions or events on the display screen.

2. A method as recited in claim 1 wherein step (a) is practiced by dividing the key words into three different classifications of words, main words that describe the most important feature of a sentence that accurately describes an aspect of a condition or event, descriptor words that further describe a main word by adding a qualification, and complements that further describe a descriptor by adding a qualification; and wherein step (b) is practiced by providing a plurality of distinctly searchable elements for each condition or event, each element including at least a main word, and where they accurately exist, a descriptor and complement associated with that main word.

3. A method as recited in claim 2 wherein the art is a medical specialty, and wherein the conditions or events are possible diseases or medical conditions of that medical specialty, and wherein the main words describe the anatomy or body fluid or tissue involved with the disease or medical condition to be addressed, the descriptor describes the deviation from normal of the main word, and the complement adds specificity to the main or descriptor words.

4. A method as recited in claim 2 wherein steps (a) and (b) are also practiced by assigning key words to laboratory test results related to each condition, including the name of a test, the normal numerical value of the test results if the condition doesn't exist, and a flag indicating that the value of inputted data is above normal, below normal, or text including at least one of normal, abnormal, positive, negative, absent, or present.

5. A method as recited in claim 1 wherein steps (a) and (b) are also practiced by assigning key words to laboratory test results related to each condition, including the name of a test, the normal numerical value of the test results if the condition doesn't exist, and a flag indicating that the value of inputted data is above normal, below normal, or text including at least one of normal, abnormal, positive, negative, absent, or present.

6. A method as recited in claim 1 wherein steps (a) and (b) are practiced by assigning either a yes or no to individual imaging possibilities related to a particular condition or event.

7. A method as recited in claim 1 comprising the further steps of providing zoom and marking functions within a displayed biopsy or image corresponding to a highlighted diagnosis upon selection of the biopsy or imaging icons.

8. A method as recited in claim 1 wherein step (c) is practiced by placing the master maps data base on a CD along with biopsy images, medical imaging images, or both biopsy images and medical imaging images, associated with a plurality of the master maps, the images capable of display on the display screen by the user manipulating the input device.

9. A method as recited in claim 1 where (c) is further practiced by displaying on the display screen at least the two conditions or events represented by master maps having the highest degree of similarity with the narrative input.

10. A method of diagnosing a condition or event from a large plurality of possible conditions or events that may exist in a particular art, each condition or event being provided in a master map which describes that condition or event using a plurality of art specific key words, said method practiced using a computer having a display screen, input device, and processor, said method comprising the steps of:
(a) providing search access to the master maps data base in the computer so that by a user manipulating the input device to provide a narrative containing some of the key words, the computer processor will compare the key words input to the key words associated with each master map;
(b) using the input device, inputting a narrative description that can facilitate diagnosis, the narrative description using some of the key words;
(c) using the input device, activating the computer processor to recognize the key words from the input narrative description, compare the key words to the key words of each of the master maps, to determine what conditions or events represented by master maps have the highest degree of similarity with the narrative input; and
(d) displaying on the display screen at least the two conditions or events represented by master maps having the highest degree of similarity with the narrative input.

11. A method as recited in claim 10 wherein each master map has key words divided into three different classifications of words, main words that describe the most important feature of a sentence that accurately describes an aspect of the condition or event associated with that master map, descriptor words that further describe a main word by adding a qualification, and complement words that further describe a descriptor by adding a qualification, each master map having a plurality of distinctly searchable elements for each condition or event, each element including at least a main word, and where they accurately exist, a descriptor and complement associated with that main word, some of the key words being weighted but the majority of key words having a common value; and wherein step (c) is practiced by counting the weighted number of key words within searchable elements in each master map which also appear in the narrative input in step (b), the master map having the highest weighted number of key words within searchable elements being determined as having the highest degree of similarity, and the condition or event associated with that master map therefore considered to have the highest probability of being the correctly diagnosed condition or event.

12. A method as recited in claim 11 wherein each master map has assigned to each of the elements one of at least two possible logics, a first logic that requires a main and at least a descriptor to also be present before the element is recognized by the processor when searching the data base, and a second logic that requires only the main to be present, but recognizes a descriptor and complement if present; and wherein step (c) is practiced by: searching with the processor for those first logic elements identified as corresponding to both main and descriptor key words in the narrative description before selection, and then counting the main, descriptor, and complement words associated with those first logic elements; and searching with the processor for those second logic elements identified as corresponding to a main key word in the narrative description and then counting the main words, and any descriptor or complement words associated therewith, of the second logic elements.

13. A method as recited in claim 10 wherein a plurality of possible conditions or events or possible diseases or medical conditions in a specialty, and steps (a) through (c) are practiced by a specialist physician.

14. A method as recited in claim 13 wherein the data base provided in step (a) also includes key words assigned to laboratory test results related to each medical condition or disease, including the name of a test, the normal numerical value of the test results, and a flag indicating that the value of inputted data is above normal, below normal, or text including at least one of normal, abnormal, positive, negative, absent, or present; and values of yes or no assigned to individual imaging possibilities related to a particular medical condition or disease; and wherein step (c) is also practiced by searching the relevant laboratory test results and imaging values.

15. A method as recited in claim 14 wherein steps (a) and (b) are practiced by assigning either a yes or no to individual imaging possibilities related to a particular condition or event.

16. A method of facilitating diagnosis of medical conditions using a computer having a display screen, an input device, and processor, and connected to a data base of detailed medical information including a plurality of master maps, one for each known medical condition to be evaluated, said method, comprising the steps of:
(a) using the keyboard, inputting into the computer a medical description of a patient's history and physical information, including signs and symptoms, using simple medical file language;
(b) displaying chemical and test data information on the screen to prompt entry of available chemical and test data for the patient;
(c) using the input device, entering all relevant chemical and test data in response to the prompt from step (b);

(d) displaying a plurality of imaging option selections on the screen in yes/no format;

(e) using the input device, entering known imaging data in yes/no format in response to the display in step (d);

(f) using the processor, searching the data base of detailed medical information to determine the degree of resemblance between the data input and each of the master maps, and ranking possible diagnoses based upon the degree of resemblance; and (g) displaying on the screen at least the two most probable diagnoses based upon the degree of resemblance determined in step (f), and in order of the degree of resemblance.

17. A method as recited in claim 16 wherein step (g) is practiced to display possible diagnoses in the form of horizontal bar graphics in which the bar graph is a first color in a horizontal field and the diagnosis corresponding to the bar graph is also in the horizontal field in a second color, different than the first color, the length of the bar graphics being proportioned to the probability of the diagnosis.

18. A method as recited in claim 16 comprising the further step (h) of displaying at least one of biopsy and imaging icons that may be selected to provide pictorial information displayed on the screen corresponding to a selected one of the diagnoses displayed on the screen.

19. A method as recited in claim 16 comprising the further steps, during the practice of at least one of steps (b) and (c), and steps (d) and (e), of displaying an alphabetical keyboard image on the screen, and using the input device selecting a letter from the alphabetical keyboard image to display on the screen listing of chemical or test data, or imaging options, starting with the letter selected.

20. A method of facilitating diagnosis of specialty related medical conditions using a computer having a display screen, input device, and processor, and connected to a data base of specialty medical information, comprising the steps of:

(a) using the input device, inputting into the computer a medical description of a patient's history and physical information, including signs and symptoms, and any relevant available chemical and test data and imaging information;

(b) using the processor searching the data base of specialty medical information to determine the most likely possible diagnosis;

(c) displaying on the screen at least the two most probable diagnoses located in step (b); and (d) substantially simultaneously with step (c), displaying on the screen textual information, and at least one of biopsy and imaging icons, corresponding to a selected diagnosis, the biopsy and imaging icons, if selected, displaying on the screen actual pictorial representations of actual biopsies or images associated with the diagnosis selected.

21. A method as recited in claim 20 comprising the further step (e) of displaying on the screen in comparative format biopsy or imaging pictorial representations corresponding to more than one diagnosis from step (c).

22. A method of providing specific categorized information relating to medical information using a computer having a display screen and input device, and connected to a data base of medical information, comprising the steps of:

(a) displaying on the screen the options of biopsy, imaging, management, and bibliography relating to a particular disease or medical condition;

(b) using the input device, selecting the biopsy option to display pictorially on the screen actual biopsy pictorial representations of the particular disease or medical condition;

(c) using the input device selecting the imaging options to display pictorially on the screen actual imaging pictorial representations of the particular disease or medical condition;

(d) using the input device selecting the management option to display on the screen a condensed opinion and textual information about how to understand and treat the particular disease or medical condition; and (e) using the input device selecting the bibliography option to display on the screen a listing of suggested readings related to pathogenesis and therapy for the particular disease or condition.

23. A method as recited in claim 22 wherein steps (b) and (c) are further practiced by displaying zoom and marking functions on the screen, and using the input device selecting the zoom or marking functions to effect an increase or decrease in the size of any particular area of the biopsy or imaging pictorial representations displayed, or to effect marking of any desired portion of the biopsy or imaging pictorial representations displayed.

24. A method of providing specific categorized information relating to medical information, using a computer having a display screen, an input device, a CD ROM, and a data base on a CD, comprising the steps of:

(a) displaying on the screen an analytical option and a catalog option;

(b) using the input device, selecting the analytical option to bring up screens allowing the input of a patient's history and physical information, including signs and symptoms, chemical and test data, and imaging data, that may contribute to an accurate differential diagnosis;

(c) using the input device entering the known information from step (b);

(d) with the computer searching the CD data base to compare the information entered with known disease and medical condition information contained in the data base;

(e) using the input device selecting the catalog option to display on the screen options relating to an opinion about how to understand and treat a disease or condition, reading material relating to a selected disease or condition, and at least one of biopsy and imaging information relating to a selected disease or condition; and (f) using the input device, selectively displaying the at least one of biopsy and imaging information from the CD in pictorial form on the display screen, which biopsy or imaging information relates to a selected disease or condition.

25. A method as recited in claim 24 wherein steps (e) and (f) are practiced to display both biopsy and imaging information relating to a selected disease or condition.

* * * * *